(12) United States Patent
Chaves et al.

(10) Patent No.: US 12,252,486 B2
(45) Date of Patent: Mar. 18, 2025

(54) SOLID STATE FORMS

(71) Applicant: Amgen Inc., Thousand Oaks, CA (US)

(72) Inventors: Mary Chaves, Arlington, MA (US); Ron C. Kelly, Westlake Village, CA (US); Prashant Agarwal, Chelsea, MA (US); Stephan D. Parent, West Lafayette, IN (US); Darren Leonard Reid, Belmont, MA (US); Roman Shimanovich, Brighton, MA (US)

(73) Assignee: Amgen Inc., Thousand Oaks, CA (US)

( * ) Notice: Subject to any disclaimer, the term of this patent is extended or adjusted under 35 U.S.C. 154(b) by 627 days.

(21) Appl. No.: 17/612,717

(22) PCT Filed: May 20, 2020

(86) PCT No.: PCT/US2020/033832
§ 371 (c)(1),
(2) Date: Nov. 19, 2021

(87) PCT Pub. No.: WO2020/236948
PCT Pub. Date: Nov. 26, 2020

(65) Prior Publication Data
US 2022/0235045 A1    Jul. 28, 2022

Related U.S. Application Data

(60) Provisional application No. 62/851,049, filed on May 21, 2019.

(51) Int. Cl.
C07D 471/04 (2006.01)
A61P 35/00 (2006.01)

(52) U.S. Cl.
CPC ............ C07D 471/04 (2013.01); A61P 35/00 (2018.01); C07B 2200/13 (2013.01)

(58) Field of Classification Search
CPC ............................... C07D 471/04; A61P 35/00
See application file for complete search history.

(56) References Cited

U.S. PATENT DOCUMENTS

| | | |
|---|---|---|
| 10,519,146 B2 | 12/2019 | Lanman et al. |
| 10,532,042 B2 | 1/2020 | Lanman et al. |
| 11,090,304 B2 | 8/2021 | Allen et al. |
| 11,236,091 B2 | 2/2022 | Chaves et al. |
| 11,285,135 B2 | 3/2022 | Lanman et al. |
| 11,827,635 B2 | 11/2023 | Chaves et al. |
| 11,905,281 B2 | 2/2024 | Lanman et al. |
| 2015/0239900 A1 | 8/2015 | Li et al. |
| 2018/0177767 A1 | 6/2018 | Lanman et al. |
| 2018/0334454 A1 | 11/2018 | Lanman et al. |
| 2019/0077801 A1 | 3/2019 | Lanman et al. |
| 2020/0055845 A1 | 2/2020 | Lanman et al. |
| 2021/0009577 A1 | 1/2021 | Lanman et al. |
| 2022/0106313 A1 | 4/2022 | Chaves et al. |
| 2022/0168280 A1 | 6/2022 | Lanman et al. |
| 2024/0067647 A1 | 2/2024 | Chaves et al. |
| 2024/0174660 A1 | 5/2024 | Lanman et al. |

FOREIGN PATENT DOCUMENTS

| | | |
|---|---|---|
| WO | 2015001076 A1 | 1/2015 |
| WO | 2015054572 A1 | 4/2015 |
| WO | 2016044772 A1 | 3/2016 |
| WO | 2016164675 A1 | 10/2016 |
| WO | 2017201161 A1 | 11/2017 |
| WO | 2018119183 A2 | 6/2018 |
| WO | 2018217651 A1 | 11/2018 |
| WO | 2019051291 A1 | 3/2019 |
| WO | 2019213516 A1 | 11/2019 |
| WO | 2020102730 A1 | 5/2020 |
| WO | 2020236947 A1 | 11/2020 |
| WO | 2020236948 A1 | 11/2020 |
| WO | 2021097207 A1 | 5/2021 |
| WO | 2021097212 A1 | 5/2021 |

OTHER PUBLICATIONS

Non-Final Office Action for U.S. Appl. No. 17/553,598, mailed Apr. 26, 2023, 4 pages.
Notice of Allowance for U.S. Appl. No. 17/553,598, mailed Aug. 9, 2023, 5 pages.
AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).
AMG-510; HY-114277; Source: MedChemexpress Mce (HY-114277); Deposit Date: May 13, 2019 Available Date: May 13, 2019; SID: 384060569[CID: 137278711] (available at https://pubchem.ncbi.nlm.nih.gov/substance/384060569).
Canon, et al., "The clinical KRAS(G12C) inhibitor AMG 510 drives anti-tumour immunity," Nature, 575(7781): 217-223 (2019) (Supplementary Material, pp. 1-55).
Canon, et al., "The clinical KRAS(G12C) inhibitor AMG 510 drives anti-tumour immunity," Nature, 575(7781): 217-223 (2019).
Dimartino et al., "Preparation and Physical Characterization of Forms II and III of Paracetamol," Journal of Thermal Analysis, 48:447-458 (1997).
Final Office Action for U.S. Appl. No. 15/984,855, mailed Mar. 28, 2019, 7 pages.
International Search Report for PCT/US2017/067801, mailed Jul. 25, 2018, 6 pages.

(Continued)

*Primary Examiner* — Rebecca L Anderson

(74) *Attorney, Agent, or Firm* — Markus Bergauer

(57) ABSTRACT

The present invention provides a crystalline form and stable salts of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, including several hydrochloride salt forms, phosphate salt form, mesylate salt form, and solid state forms thereof, pharmaceutical compositions, and methods of treating a disease mediated by KRAS G12C inhibition.

54 Claims, 14 Drawing Sheets

(56) References Cited

OTHER PUBLICATIONS

International Search Report for PCT/US2018/033714, mailed Jul. 17, 2018, 3 pages.
International Search Report for PCT/US2019/061815, mailed Mar. 5, 2020, 6 pages.
International Search Report for PCT/US2020/033831, mailed Jul. 9, 2020, 6 pages.
International Search Report for PCT/US2020/033832, mailed Jul. 8, 2020, 4 pages.
International Search Report for PCT/US2020/060415, mailed Feb. 3, 2021, 7 pages.
International Search Report for PCT/US2020/060421, mailed Feb. 18, 2021, 4 pages.
Lanman, et al., "Discovery of a Covalent Inhibitor of KRAS$^{G12C}$ (AMG 510) for the Treatment of Solid Tumors," *J. Med. Chem.*, 63: 52-65 (2020).
Non-Final Office Action for U.S. Appl. No. 15/984,855, mailed Sep. 27, 2018, 25 pages.
Noriaki Hirayama, "Handbook for Making Crystal of Organic Compound,—Principles and Know-how—", Maruzen Co., Ltd., Jul. 25, 2008, pp. 57-84.
Noriyuki Takada, "API Form Screening and Selection at the Drug Discovery Stage", Pharm Stage, vol. 6, No. 10, Jan. 15, 2007, pp. 20-25.
Takashi Kojima, "Aiming to Improve the Efficiency of Crystallization Selection in Drug Development", Pharmaceutics, Sep. 1, 2008, vol. 68, No. 5, pp. 344-349.
Third Party Observation filed for PCT/US2020/033831, submitted Jan. 15, 2021, 2 pages.
Written Opinion for PCT/US2017/067801, mailed Jul. 25, 2018, 10 pages.
Written Opinion for PCT/US2018/033714, mailed Jul. 17, 2018, 5 pages.
Written Opinion for PCT/US2019/061815, mailed Mar. 5, 2020, 4 pages.
Written Opinion for PCT/US2020/033831, mailed Jul. 9, 2020, 7 pages.
Written Opinion for PCT/US2020/033832, mailed Jul. 8, 2020, 6 pages.
Written Opinion for PCT/US2020/060415, mailed Feb. 3, 2021, 9 pages.
Written Opinion for PCT/US2020/060421, mailed Feb. 18, 2021, 5 pages.
International Search Report for PCT/US2019/030593, mailed Aug. 6, 2019, 4 pages.
Written Opinion for PCT/US2019/030593, mailed Aug. 6, 2019, 5 pages.
Knapman, "Polymorphic Predictions: Understanding the nature of crystalline compounds can be critical in drug development and manufacture", *Modern Drug Discovery*, 53-57 (2000).
Brittain et al. (Editor), "Polymorphism in Pharmaceutical Solids," Chapters 1 and 5, Marcel Dekker, 1999 (95 pages).
Byrn et al., "Pharmaceutical solids: a strategic approach to regulatory considerations," Pharm. Res. 12(7):945-954 (1995).
Caira, "Crystalline Polymorphism of Organic Compounds," in Design of Organic Solids, Topics in Current Chemistry 198, Weber (Ed.) Springer, Berlin Heidelberg, 163-208 (1998).
Kojima et al., "Optimization of development format in drug development", Pharmacia, 387-391 (2016) (including English abstract).
Ono, "Present state analysis of salt selection", Journal of Pharmaceutical Science and Technology, 176-182 (2013) (including Google Machine Translation).
Shah et al., "Approaches for Improving Bioavailability of Poorly Soluble Drugs," in AUGSBURGER and HOAG, "Pharmaceutical Dosage Forms - Tablets: Rational Design and Formulation", CRC Press, vol. 2, Chapter 2, pp. 51-104 (2008).

SOLID STATE FORMS

CROSS REFERENCES TO RELATED APPLICATIONS

This application is a national stage application under 35 U.S.C. § 371 of International Application No. PCT/US2020/033832, having an international filing date of May 20, 2020, which claims the benefit of U.S. Provisional Application No. 62/851,049, filed on May 21, 2019, each of which is incorporated by reference herein in its entirety.

FIELD

The present disclosure provides at least one crystalline salt form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, (hereinafter "Compound 1"), including several crystalline forms of a hydrochloride salt form, a phosphate salt form, and a mesylate salt form, pharmaceutical compositions, and a method of treating a disease mediated by KRAS G12C inhibition.

BACKGROUND

Compound 1 is a selective inhibitor of KRAS G12C useful for the treatment of cancers, including treatment of lung cancer, such as non-small cell lung cancer (NSCLC), pancreatic cancer, and colorectal cancer. United States Patent Application Publication Number 2018/0334454A1, published on Nov. 22, 2018, discloses Compound 1.

Many compounds can exist in different crystal forms, or polymorphs, which exhibit different physical, chemical, and spectroscopic properties. For example, certain polymorphs of a compound may be more readily soluble in particular solvents, may flow more readily, or may compress more easily than others. See, e.g., P. DiMartino, et al., *J. Thermal Anal.,* 48:447-458 (1997). In the case of drugs, certain solid forms may be more bioavailable than others, while others may be more stable under certain manufacturing, storage, and biological conditions. This is particularly important from a regulatory standpoint, since drugs are approved by agencies such as the U.S. Food and Drug Administration only if they meet exacting purity and characterization standards. Indeed, the regulatory approval of one polymorph of a compound, which exhibits certain solubility and physicochemical (including spectroscopic) properties, typically does not imply the ready approval of other polymorphs of that same compound.

Polymorphic forms of a compound are known in the pharmaceutical arts to affect, for example, the solubility, stability, flowability, fractability, and compressibility of the compound, as well as the safety and efficacy of drug products comprising it. See, e.g., Knapman, K. *Modern Drug Discoveries,* 2000, 53. Therefore, the discovery of new polymorphs of a drug can provide a variety of advantages.

The present disclosure provides new polymorphic forms of Compound 1, including several crystalline salt forms, and physical forms thereof, pharmaceutical compositions, and a method of treating a disease mediated by KRAS G12C inhibition. The new polymorphic forms can further the development of formulations for the treatment of these chronic illnesses, and may yield numerous formulation, manufacturing and therapeutic benefits.

SUMMARY

The present disclosure provides stable crystalline forms of Compound 1, including several crystalline forms of a hydrochloride salt form, a phosphate salt form, and a mesylate salt form, pharmaceutical compositions, and a method of treating a disease mediated by KRAS G12C inhibition.

DETAILED DESCRIPTION

Definitions

Figure 1:
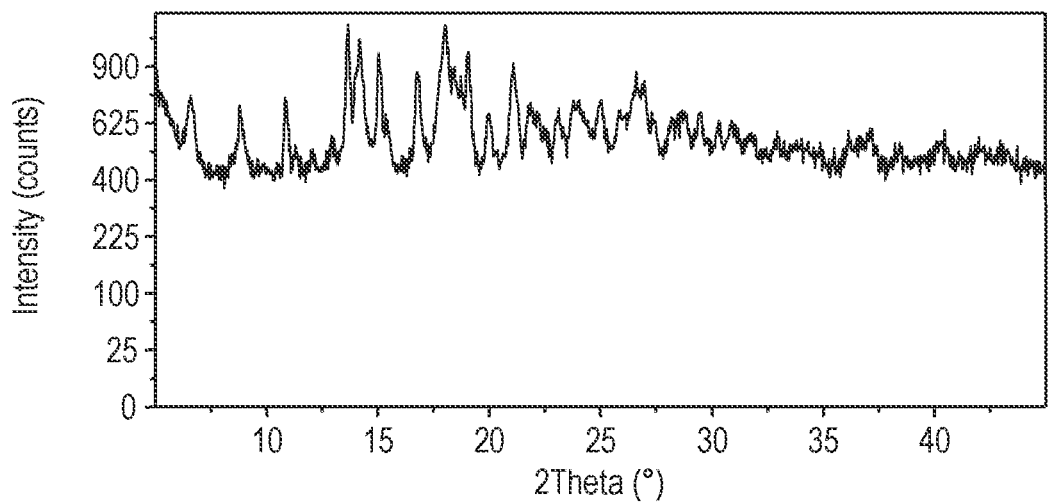
FIG. 1 shows XRPD data for the hydrochloride salt Form I of Compound 1. The powder X-ray diffraction pattern of the hydrochloride salt Forms I-VII of Compound 1 is characteristic of crystalline material with distinct diffraction peaks between 3° 2-theta to 40° 2-theta.

The term "Compound 1" means 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

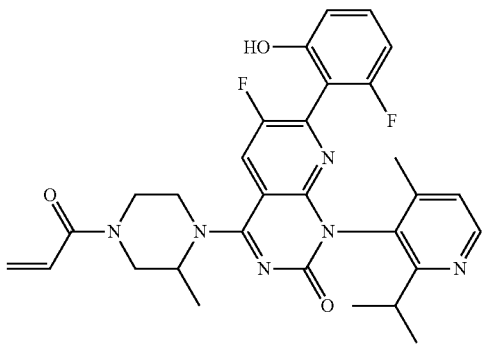

Chemical Formula: $C_{30}H_{30}F_2N_6O_3$
Exact Mass: 560.23
Molecular Weight: 560.61
Elemental Analysis:
C, 64.28; H, 5.39; F, 6.78; N, 14.99; O, 8.56

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. For example, Compound 1 is

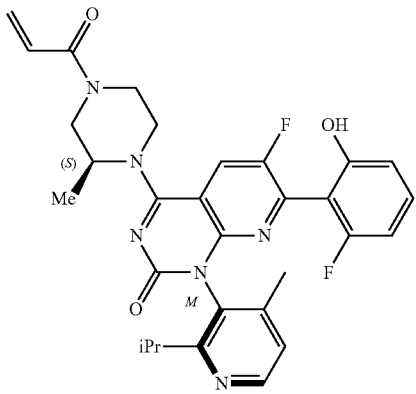

atropisomer M and may exhibit restricted rotation. The M-atropisomer of Compound 1 is also known as AMG 510. Canon, J., et al., *Nature* 575(7781):217-223 (2019), FIG. 1a.

Alternatively, Compound 1 has the following atropisomer P and may exhibit restricted rotation.

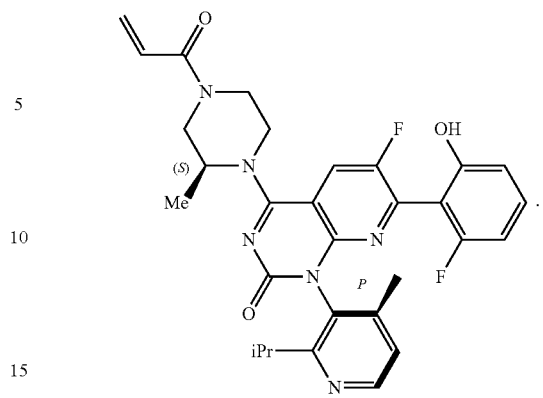

Abbreviation: The following abbreviation may be used herein:

| | |
|---|---|
| AcOH | acetic acid |
| aq or aq. | aqueous |
| DCM | dichloromethane |
| DME | 1,2-dimethoxyethane |
| DMF | N,N-dimethylformamide |
| DMSO | dimethyl sulfoxide |
| eq or eq. or equiv. | equivalent |
| ESI or ES | electrospray ionization |
| Et | ethyl |
| Et$_2$O | diethyl ether |
| EtOAc | ethyl acetate |
| EtOH | ethanol |
| g | gram(s) |
| h | hour(s) |
| HPLC | high pressure liquid chromatography |
| IPA | Isopropyl alcohol |
| iPr | isopropyl |
| iPr$_2$NEt or DIPEA | N-ethyl diisopropylamine (Hünig's base) |
| LC MS, LCMS, LC-MS or LC/MS | liquid chromatography mass spectroscopy |
| LG | leaving group (e.g., halogen, mesylate, triflate) |
| m/z | mass divided by charge |
| Me | methyl |
| MeCN | acetonitrile |
| MeOH | Methanol |
| MEK | Methyl ethyl ketone |
| Met | metal species for cross-coupling (e.g., MgX, ZnX, SnR$_3$, SiR$_3$, B(OR)$_2$) |
| mg | milligrams |
| min | minutes |
| mL | milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| Pd$_2$(dba)$_3$ | tris(dibenzylideneacetone)dipalladium(0) |
| Pd(dppf)Cl$_2$•DCM, Pd(dppf)Cl$_2$ | [1,1'-bis(diphenylphosphino)ferrocene]dichloropalladium(II), complex with dichloromethane |
| Pd(PPh$_3$)$_4$ | tetrakis(triphenylphosphine)palladium(0) |
| Ph | phenyl |
| ppm | parts per million |
| PR or PG or Prot. group | protecting group |
| rbf | round-bottomed flask |
| RP-HPLC | reverse phase high pressure liquid chromatography |
| RT or rt or r.t. | room temperature |
| sat. or satd. | saturated |
| SFC | supercritical fluid chromatography |
| SPhos Pd G3 or SPhos G3 | (2-dicyclohexylphosphino-2',6'-dimethoxybiphenyl) [2-(2'-amino-1,1'-biphenyl)]palladium(II) methanesulfonate |
| SSNMR | Solid state nuclear magnetic resonance |
| TBAF | tetra-n-butylammonium fluoride |

| | -continued |
|---|---|
| TBTU | N,N,N',N'-tetramethyl-O-(benzotriazol-1-yl)uronium tetrafluoroborate |
| t-BuOH | tert-butanol |
| TEA or Et₃N | trimethylamine |
| TFA | trifluoroacetic acid |
| THF | tetrahydrofuran |
| UV | ultraviolet |

The use of the terms "a," "an," "the," and similar referents in the context of the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the invention unless otherwise claimed. No language in the specification should be construed as indicating any non-claimed element as essential to the practice of the invention.

The term "anhydrous form of Compound 1" means a form of Compound 1 substantially or completely free from water and particularly water of crystallization. Those skilled in the art appreciate that the exact number of water molecules may vary slightly at any time with variable temperature, pressure, and other environmental influences. All slight variations of the number of the associated water molecules are contemplated to be within the scope of the present disclosure.

The term "co-crystal" means a crystalline material comprising two or more compounds at ambient temperature (20° C. to 25'° C., preferably 20° C.), of which at least two are held together by weak interaction, wherein at least one of the compounds is a co-crystal former and the other is Compound 1. Weak interaction is being defined as an interaction which is neither ionic nor covalent and includes for example: hydrogen bonds, van der Waals forces, and π-π interactions. The term "co-crystal" includes solvate forms.

The term "amorphous form" or "amorphous" means a material that lacks long range order and as such does not show distinct X-ray diffraction peaks, i.e. a Bragg diffraction peak. The XRPD pattern of an amorphous material is characterized by one or more amorphous halos.

The term "amorphous halo" is an approximately bell-shaped maximum in the X-ray powder pattern of an amorphous substance.

The term "excipient" means any pharmaceutically acceptable additive, carrier, diluent, adjuvant, or other ingredient, other than the active pharmaceutical ingredient (API), which is typically included for formulation and/or administration to a patient.

The term "a disease mediated by KRAS G12C inhibition" means (i) cancers and (ii) solid tumors. KRAS is the most frequently mutated oncogene in cancer and encodes a key signalling protein in tumours. Canon, J., et al., *Nature* 575(7781):217-223 (2019), abstract. The KRAS (G12C) mutant has a cysteine residue that has been exploited to design covalent inhibitors that have promising preclinical activity. Id A series of inhibitors was optimized, using novel binding interactions to markedly enhance their potency and selectivity. Id. The efforts have led to the discovery of AMG 510. Id In preclinical analyses, treatment with AMG 510 led to the regression of KRAS$^{G12C}$ tumors and improved the anti-tumor efficacy of chemotherapy and targeted agents. Id. In immune-competent mice, treatment with AMG 510 resulted in a pro-inflammatory tumor microenvironment and produced durable cures alone as well as in combination with immune-checkpoint inhibitors. Id. Cured mice rejected the growth of isogenic KRAS$^{G12D}$ tumors, which suggests adaptive immunity against shared antigens. Id Furthermore, in clinical trials, AMG 510 demonstrated anti-tumor activity in the first dosing cohorts and represents a potentially transformative therapy for patients for whom effective treatments are lacking. Id.

The term "cancer" means a hyperproliferative disorder in a mammal, such as a human, with a KRAS, HRAS or NRAS G12C mutation, which can be treated by, for example, by administering to said mammal a therapeutically effective amount of Compound 1 as disclosed herein. In some embodiments, the cancer is, for example, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urachal cancer, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

The term "patient" means animals, such as dogs, cats, cows, horses, sheep and humans. Particular patients are mammals. The term patient includes males and females.

The term "therapeutically effective amount" means an amount of a compound that ameliorates, attenuates or eliminates one or more symptom of a particular disease or condition, or prevents or delays the onset of one of more symptoms of a particular disease or condition.

The term "pharmaceutically acceptable" means that the referenced substance, such as a compound of the present disclosure or a formulation containing a compound of the present disclosure, or a particular excipient, are suitable for administration to a patient.

As used herein and unless otherwise indicated, the terms "polymorph" and "polymorphic form" refer to solid crystalline forms of a compound or complex. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid state nuclear magnetic resonance (NMR), infrared (IR) spectroscopy, Raman spectroscopy, hot stage optical microscopy, scanning electron microscopy (SEM), electron crystallography and quantitative analysis, particle size analysis (PSA), surface area analysis, solubility, and rate of dissolution.

As used herein to refer to the spectra or data presented in graphical form (e.g., XRPD, IR, Raman and NMR spectra), and unless otherwise indicated, the term "peak" refers to a peak or other special feature that one skilled in the art would recognize as not attributable to background noise.

As used herein and unless otherwise indicated, the term "substantially pure" when used to describe a polymorph of a compound means a solid form of the compound that comprises that polymorph and is substantially free of other polymorphs of the compound. A representative substantially pure polymorph comprises greater than about 80% by weight of one polymorphic form of the compound and less than about 20% by weight of other polymorphic forms of the compound, more preferably greater than about 90% by weight of one polymorphic form of the compound and less than about 10% by weight of the other polymorphic forms of the compound, even more preferably greater than about 95% by weight of one polymorphic form of the compound and less than about 5% by weight of the other polymorphic forms of the compound, and most preferably greater than about 97% by weight of one polymorphic forms of the compound and less than about 3% by weight of the other polymorphic forms of the compound.

The terms "treating", "treat" or "treatment" and the like include preventative (e.g., prophylactic) and palliative treatment.

The term "variable hydrate" means a hydrate of Compound 1 having at least about one, two, three, or four associated water molecules. In some embodiments, the hydrates of the present disclosure include from at least one to ten associated molecules of water. Those skilled in the art appreciate that the exact number of the associated water molecules may vary slightly at any time with variable temperature, pressure, and other environmental influence. All slight variations of the number of the associated water molecules are contemplated to be within the scope of the present disclosure.

In some embodiments, the methods for treatment are directed to treating lung cancers, the methods comprise administering an effective amount of any of the above described compounds (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas. In one embodiment the NSCLC is locally advanced or metastatic.

The compounds of the present disclosure are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied overtime.

In addition, the compounds of the present disclosure can be administered alone, in combination with other compounds of the present disclosure, or with other pharmaceutically active compounds. The other pharmaceutically active compounds can be intended to treat the same disease or condition as the compounds of the present disclosure or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

It is also noted that the solid state forms of the present disclosure can be administered together. For example, substantially pure crystalline anhydrous form I of Compound 1 can be administered to a patient. Alternatively, about 90% by weight of crystalline anhydrous form I of Compound 1 can be administered with the remaining Compound 1 present in other forms, such as the amorphous form of Compound I. In another embodiment, 80% by weight of crystalline anhydrous form I of Compound 1 can be administered with the remaining Compound 1 present in other forms, such as the amorphous form. All combinations are contemplated. In one embodiment of the disclosure, Compound 1 is administered to a patient in one substantially pure form. Those skilled in the art will appreciate the possible variations.

The compounds of the present disclosure may be used in the manufacture of a medicament for the treatment of a disease mediated by KRAS G12C inhibition, such as cancer, including but not limited to colorectal cancer, pancreatic cancer and lung cancer, such as non-small cell lung cancer (NSCLC).

In still a further aspect, the disclosure relates to the use of a salt, a crystalline form, an amorphous form, or co-crystal of Compound 1 for the preparation of a medicament useful for treating cancer, such as colorectal cancer, pancreatic cancer and lung cancer, such as non-small cell lung cancer (NSCLC).

Since one aspect of the present disclosure contemplates the treatment of the disease/conditions with a combination of pharmaceutically active compounds that may be administered separately, the disclosure further relates to combining separate pharmaceutical compositions in kit form. The kit comprises two separate pharmaceutical compositions: a compound of the present disclosure, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present disclosure can consist of one tablet or capsule, while a daily dose of the second compound can consist of several tablets or capsules and vice versa. The memory aid should reflect this and aid in correct administration of the active agents.

In another specific embodiment of the disclosure, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present disclosure and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated. In one embodiment, the compounds of the present disclosure and other pharmaceutically active compounds, if desired, can be administered to a patient orally.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. In one embodiment the dosage form contemplated in this disclosure is a solid dosage for, such as a tablet for oral administration.

Solid compositions of a similar type may also be used as fillers in hard filled gelatin capsules using such excipients as lactose, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs, for example in a soft filled gelatin capsules. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present disclosure include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this disclosure.

The compounds of the present disclosure can be administered to a patient at dosage levels in the range of about 0.1 to about 2000 mg per day, preferably from 5 mg to 1000 mg per day. For a normal adult human having a body weight of about 70 kg, a dosage in the range of about 0.001 mg per kilogram body weight to about 20 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

Unless specifically stated otherwise, the compounds of the present disclosure may exist in unsolvated as well as solvated forms with pharmaceutically acceptable solvents such as water (hydrate), ethanol, and the like. The present disclosure contemplates and encompasses both the solvated and unsolvated forms.

It is also possible that compounds of the present disclosure may exist in different tautomeric forms. All tautomers of compounds of the present disclosure are contemplated. For example, all keto-enol forms of the compounds are included in this disclosure.

Those skilled in the art will recognize that the compound names and structures contained herein may be based on a particular tautomer of a compound. While the name or structure for only a particular tautomer may be used, it is intended that all tautomers are encompassed by the present disclosure, unless stated otherwise.

Those skilled in the art will understand that the anhydrous free forms, hydrates, salts and co-crystals of Compound 1 may exist in one or more ionization states. which typically exists as zwitterions. While the name or structure for only a particular ionization state may be used, it is intended that all ionization states are encompassed by the present disclosure, unless stated otherwise.

It is also intended that the present disclosure encompass compounds that are synthesized in vitro using laboratory techniques, such as those well known to synthetic chemists; or synthesized using in vivo techniques, such as through metabolism, fermentation, digestion, and the like. It is also contemplated that the compounds of the present disclosure may be synthesized using a combination of in vitro and in vivo techniques.

The present disclosure also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present disclosure that contain the aforementioned isotopes and/or other isotopes of other atoms are within the scope of this disclosure. Certain isotopically-labelled compounds of the present disclosure, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this disclosure can generally be prepared by substituting a readily available isotopically labelled reagent for a non-isotopically labelled reagent.

All patents and other publications recited herein are hereby incorporated by reference.

The examples and embodiments presented below are illustrative of the invention disclosed herein and are not intended to limit the scope of the claims in any manner.

EMBODIMENTS

1. In one embodiment of the present disclosure, the present disclosure provides a crystalline hydrochloride salt form I of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

2. In another embodiment of the present disclosure, the present disclosure provides the crystalline anhydrous form I of claim 1, wherein the hydrochloride salt form I is the M atropisomer.

3. In another embodiment of the present disclosure, the present disclosure provides the crystalline hydrochloride salt form I of claim 1, wherein the hydrochloride salt form I is characterized by the powder X-ray diffraction pattern substantially as shown in FIG. 1.

4. In another embodiment of the present disclosure, the present disclosure provides the crystalline hydrochloride salt form I of Compound 1 of claim 1, wherein said form is characterized by at least three peaks, at least five peaks, or at least seven peaks selected from a powder X-ray diffraction pattern comprising peaks at diffraction angle 2 theta degrees at approximately 6.6, 8.9, 10.9, 13.7, 14.2, 15.1, 16.8 18.0, 19.0, and 21.1.

5. In another embodiment of the present disclosure, the present disclosure provides the crystalline hydrochloride salt form I of Compound 1 of claim 1, wherein said form is characterized by a powder X-ray diffraction pattern comprising peaks at diffraction angle 2 theta degrees at approximately 8.9, 10.9 and 14.2.

6. In another embodiment of the present disclosure, the present disclosure provides the crystalline hydrochloride salt form I of Compound 1 of claim 1 having a differential scanning calorimetry thermogram comprising an endotherm with an onset of about 192° C.

7. In another embodiment of the present disclosure, the present disclosure provides the crystalline hydrochloride salt form I of Compound 1 of claim 1 having a thermogravimetric analysis thermogram comprising a weight loss of about 0.2% to about 5.3% when heated from about 30° C. to about 150° C.

8. In another embodiment of the present disclosure, the present disclosure provides the crystalline hydrochloride salt form I of claim 1 which is substantially pure.

9. In another embodiment of the present disclosure, the present disclosure provides a pharmaceutical composition comprising the crystalline hydrochloride salt form I of claim 1, and a pharmaceutically acceptable excipient.

10. In another embodiment of the present disclosure, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the hydrochloride salt form I of claim 1.

11. In another embodiment of the present disclosure, the present disclosure provides the pharmaceutical composition comprising the crystalline hydrochloride salt form I as in any one of claims 1, 2, 3, 4, 5, 6, 7, 8, 9 or 10 or a mixture thereof, and a pharmaceutically acceptable excipient.

12. In another embodiment of the present disclosure, the present disclosure provides the pharmaceutical composition of claim 11, wherein the composition is a single dose.

13. In another embodiment of the present disclosure, the present disclosure provides a method for preparing the crystalline hydrochloride salt form I of claim 1, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, hydrochloric acid, and a suitable solvent to form the crystalline hydrochloride salt form I of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

14. In another embodiment of the present disclosure, the present disclosure provides the method of claim 12 wherein the suitable solvent is ethyl acetate.

15. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline hydrochloride salt form I of claim 1.

16. In another embodiment of the present disclosure, the present disclosure provides the method of claim 15, wherein said disease mediated by KRAS G12C inhibition is cancer.

17. In another embodiment of the present disclosure, the present disclosure provides the method of claim 16, wherein the cancer is lung cancer, pancreatic cancer or colorectal cancer.

18. In another embodiment of the present disclosure, the present disclosure provides the method of claim 17, wherein the cancer is lung cancer.

19. In another embodiment of the present disclosure, the present disclosure provides the method of claim 18, wherein the lung cancer is non-small cell lung cancer.

20. In another embodiment of the present disclosure, the present disclosure provides a crystalline hydrochloride salt form II of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

21. In another embodiment of the present disclosure, the present disclosure provides the crystalline hydrochloride salt form II of Compound 1 of claim 20, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one is the M atropisomer.

Figure 4:
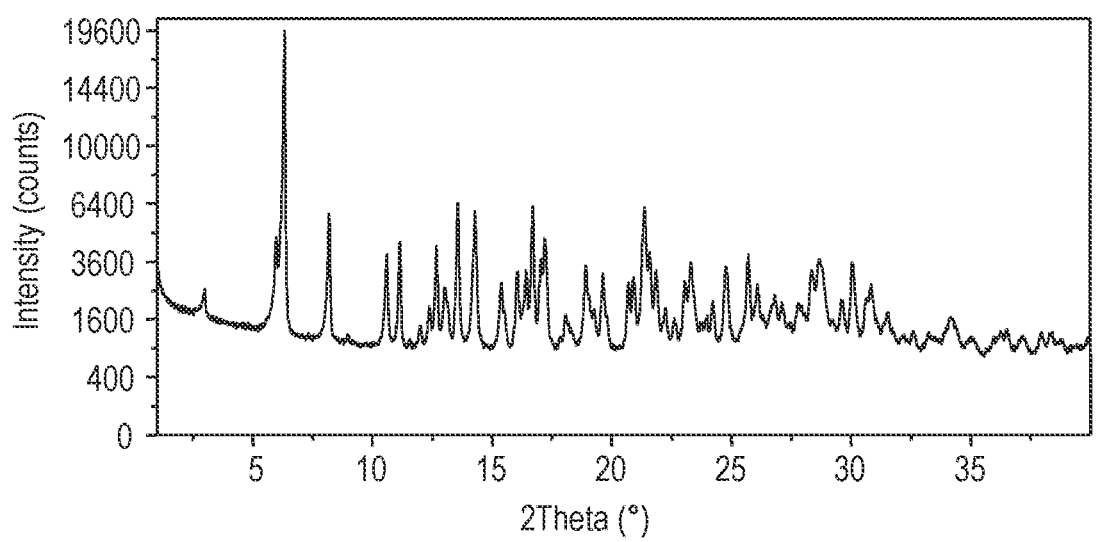
FIG. 4 shows XRPD data for the crystalline hydrochloride salt Form II of Compound 1.

22. In another embodiment of the present disclosure, the present disclosure provides the crystalline hydrochloride salt form II of claim 20, characterized by the powder X-ray diffraction pattern substantially as shown in FIG. 4.

23. In another embodiment of the present disclosure, the present disclosure provides the crystalline hydrochloride salt form II of Compound 1 of claim 20, wherein said form II is characterized by at least three peaks, at least five peaks, or at least seven peaks selected from a powder X-ray diffraction pattern comprising peaks at diffraction angle 2 theta degrees at approximately 6.0, 6.3, 8.2, 10.6, 11.2, 12.7, 13.6, 14.3, 16.1, 16.5, 17.2, 21.6 and 21.4.

24. In another embodiment of the present disclosure, the present disclosure provides the crystalline hydrochloride salt form II of Compound 1 of claim 20, wherein said form II is characterized by a powder X-ray diffraction pattern comprising peaks at diffraction angle 2 theta degrees at approximately 6.3, 8.2, 10.6, and 16.1.

25. In another embodiment of the present disclosure, the present disclosure provides the crystalline hydrochloride salt form II of Compound 1 of claim 20, having a differential scanning calorimetry thermogram comprising an endotherm with an onset of about 114° C.

26. In another embodiment of the present disclosure, the present disclosure provides the crystalline hydrochloride salt form II of Compound 1 of claim 20 having a thermogravimetric analysis thermogram comprising a weight loss of about 9% when heated from about 20° C. to about 90° C.

27. In another embodiment of the present disclosure, the present disclosure provides the crystalline hydrochloride salt form II of claim 20, which is substantially pure.

28. In another embodiment of the present disclosure, the present disclosure provides a pharmaceutical composition comprising the crystalline hydrochloride salt form II of claim 20, and a pharmaceutically acceptable excipient.

29. In another embodiment of the present disclosure, the present disclosure provides a composition comprising an amorphous form 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the hydrochloride salt form II of claim 20.

30. In another embodiment of the present disclosure, the present disclosure provides a pharmaceutical composition comprising the crystalline hydrochloride salt form I as in any one of claims 20, 21, 22, 23, 24, 25, 26, 27, 28 and 29 or a mixture thereof, and a pharmaceutically acceptable excipient.

31. In another embodiment of the present disclosure, the present disclosure provides the pharmaceutical composition of claim 30, wherein the composition is a single dose.

32. In another embodiment of the present disclosure, the present disclosure provides a method for preparing the crystalline hydrochloride salt form II of claim 20, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, HCl and a suitable solvent to form a crystalline hydrochloride salt form II of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

33. In another embodiment of the present disclosure, the present disclosure provides the method of claim 32 wherein the suitable solvent is methanol.

34. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline hydrochloride salt form II of claim 20.

35. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 30.

36. In another embodiment of the present disclosure, the present disclosure provides the method of claim 35, wherein said disease mediated by KRAS G12C inhibition is cancer.

37. In another embodiment of the present disclosure, the present disclosure provides the method of claim 36, wherein the cancer is lung cancer, pancreatic cancer or colorectal cancer.

38. In another embodiment of the present disclosure, the present disclosure provides the method of claim 37, wherein the cancer is lung cancer.

39. In another embodiment of the present disclosure, the present disclosure provides the method of claim 38, wherein the lung cancer is non-small cell lung cancer.

40. In another embodiment of the present disclosure, the present disclosure provides a crystalline hydrochloride salt form III of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

41. In another embodiment of the present disclosure, the present disclosure provides the crystalline hydrochloride salt form III of Compound 1 of claim 40, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one is the M atropisomer.

Figure 7:
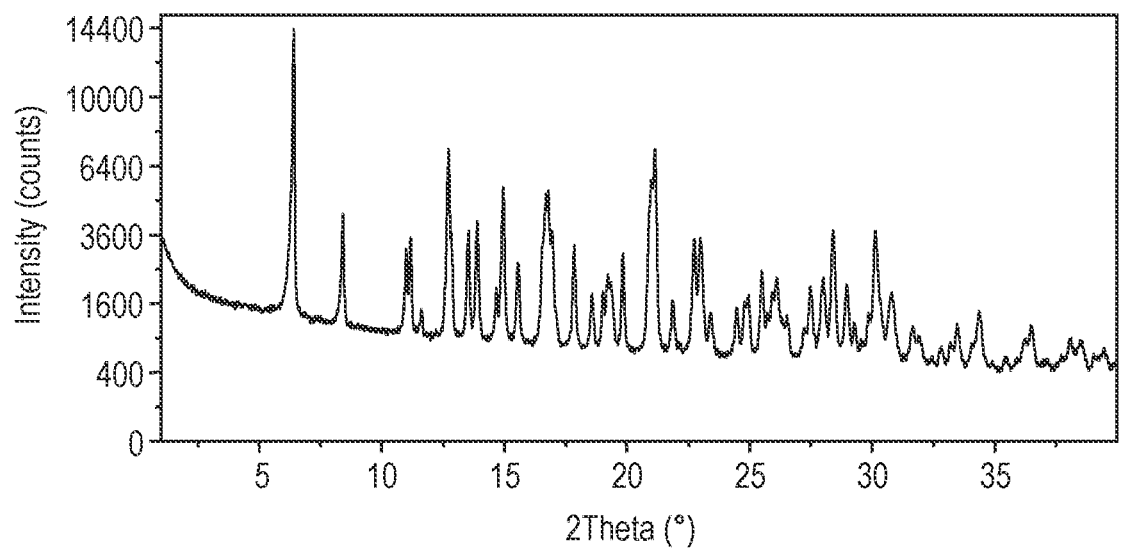
FIG. 7 shows XRPD data for the crystalline hydrochloride salt Form III of Compound 1.

42. In another embodiment of the present disclosure, the present disclosure provides the crystalline hydrochloride salt form III of claim 40, characterized by the powder X-ray diffraction pattern substantially as shown in FIG. 7.

43. In another embodiment of the present disclosure, the present disclosure provides the crystalline hydrochloride salt form III of Compound 1 of claim 40, wherein said form III is characterized by at least three peaks, at least five peaks, or at least seven peaks selected from a powder X-ray diffraction pattern comprising peaks at diffraction angle 2 theta degrees at approximately 6.4, 8.4, 11.0, 11.2, 12.7, 13.6, 13.9, 15.0, 15.6, 16.6, 16.7, 16.8, and 21.2.

44. In another embodiment of the present disclosure, the present disclosure provides the crystalline hydrochloride salt form III of Compound 1 of claim 40, wherein said form III is characterized by a powder X-ray diffraction pattern comprising peaks at diffraction angle 2 theta degrees at approximately 6.4, 8.4, 11.0, or 15.6.

45. In another embodiment of the present disclosure, the present disclosure provides the crystalline hydrochloride salt form III of Compound 1 of claim 40 having a differential scanning calorimetry thermogram comprising an endotherm with an onset of about 129° C.

46. In another embodiment of the present disclosure, the present disclosure provides the crystalline hydrochloride salt form III of Compound 1 of claim 40, having a thermogravimetric analysis thermogram comprising a weight loss of about 8% when heated from about 20° C. to about 200° C.

47. In another embodiment of the present disclosure, the present disclosure provides the crystalline hydrochloride salt form III of Compound 1 of claim 40, which is substantially pure.

48. In another embodiment of the present disclosure, the present disclosure provides a pharmaceutical composition comprising the crystalline hydrochloride salt form III of claim 40,and a pharmaceutically acceptable excipient.

49. In another embodiment of the present disclosure, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline hydrochloride salt form III of claim 1.

50. In another embodiment of the present disclosure, the present disclosure provides a pharmaceutical composition comprising the crystalline hydrochloride salt form III as in any one of claims 40, 41, 42, 43, 44, 45, 46, 47, 48 or 49, or a mixture thereof, and a pharmaceutically acceptable excipient.

51. In another embodiment of the present disclosure, the present disclosure provides the pharmaceutical composition of claim 50, wherein the composition is a single dose.

52. In another embodiment of the present disclosure, the present disclosure provides a method for preparing the crystalline hydrochloride salt form III of claim 40, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, HCl and a suitable solvent to form a crystalline hydrochloride salt form III of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

53. In another embodiment of the present disclosure, the present disclosure provides the method of claim 52 wherein the suitable solvent is dichloromethane, ethanol, ethanol/water, or n-butanol.

54. In another embodiment of the present disclosure, the present disclosure provides the method of claim 53, wherein the solvent is dichloromethane.

55. In another embodiment of the present disclosure, the present disclosure provides the method of claim 53, wherein the solvent is ethanol.

56. In another embodiment of the present disclosure, the present disclosure provides the method of claim 53, wherein the solvent is ethanol/water.

57. In another embodiment of the present disclosure, the present disclosure provides the method of claim 53, wherein the solvent is n-butanol.

58. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline hydrochloride salt form III of claim 40.

59. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 50.

60. In another embodiment of the present disclosure, the present disclosure provides the method of claim 58, wherein said disease mediated by KRAS G12C inhibition is cancer.

61. In another embodiment of the present disclosure, the present disclosure provides the method of claim 60, wherein the cancer is lung cancer, pancreatic cancer or colorectal cancer.

62. In another embodiment of the present disclosure, the present disclosure provides the method of claim 61, wherein the cancer is lung cancer.

63. In another embodiment of the present disclosure, the present disclosure provides the method of claim 62, wherein the lung cancer is non-small cell lung cancer.

64. In another embodiment of the present disclosure, the present disclosure provides a crystalline hydrochloride salt form IV of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

65. In another embodiment of the present disclosure, the present disclosure provides the crystalline hydrochloride salt form IV of Compound 1 of claim 64, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one is the M atropisomer.

Figure 10:
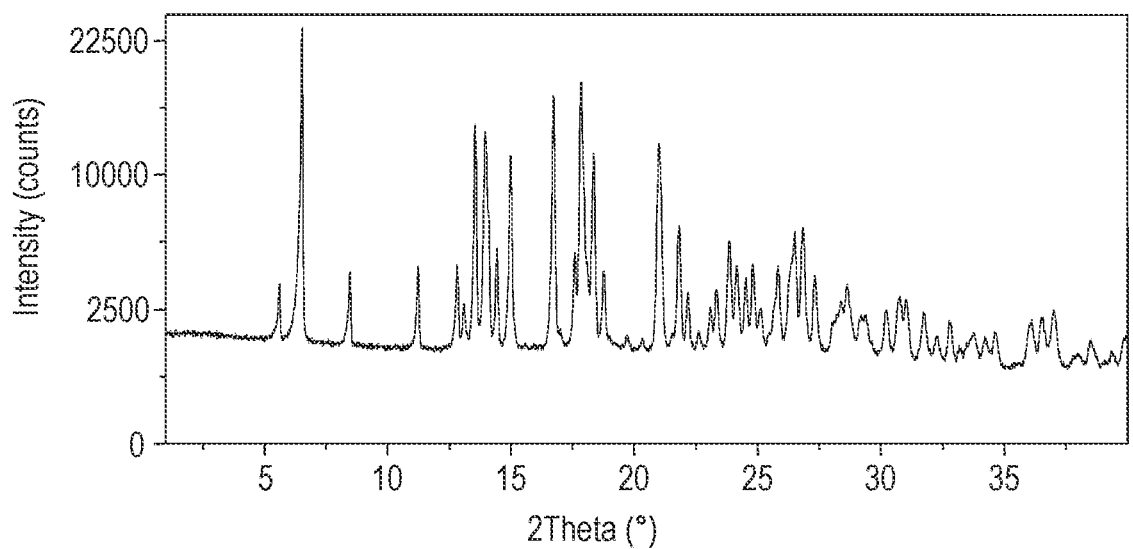
FIG. 10 shows XRPD data for the crystalline hydrochloride salt Form IV of Compound 1.

66. In another embodiment of the present disclosure, the present disclosure provides the crystalline hydrochloride salt form IV of claim 64, characterized by the powder X-ray diffraction pattern substantially as shown in FIG. 10.

67. In another embodiment of the present disclosure, the present disclosure provides the form of the crystalline hydrochloride salt form IV of Compound 1 of claim 64, wherein said form IV is characterized by at least three peaks, at least five peaks, or at least seven peaks selected from a powder X-ray diffraction pattern comprising peaks at diffraction angle 2 theta degrees at approximately 5.6, 6.5, 8.5, 11.3, 12.8, 13.6, 14.0, 14.1, 15.0, 16.7, 17.8 and 18.4.

68. In another embodiment of the present disclosure, the present disclosure provides the crystalline hydrochloride salt form IV of Compound 1 of claim 46, wherein said form IV is characterized by a powder X-ray diffraction pattern comprising peaks at diffraction angle 2 theta degrees at approximately 5.6, 6.5 and 8.5.

69. In another embodiment of the present disclosure, the present disclosure provides the crystalline hydrochloride salt form IV of Compound 1 of claim 64 having a differential scanning calorimetry thermogram comprising an endotherm with an onset of about 223° C.

70. In another embodiment of the present disclosure, the present disclosure provides the crystalline hydrochloride salt form IV of Compound 1 of claim 64, having a thermogravimetric analysis thermogram comprising a weight loss of about 4.4% when heated from about 25° C. to about 200° C.

71. In another embodiment of the present disclosure, the present disclosure provides the crystalline hydrochloride salt form IV of claim 64 which is substantially pure.

72. In another embodiment of the present disclosure, the present disclosure provides a pharmaceutical composition comprising the crystalline hydrochloride salt form IV of claim 64, and a pharmaceutically acceptable excipient.

73. In another embodiment of the present disclosure, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline hydrochloride salt form IV of claim 64.

74. In another embodiment of the present disclosure, the present disclosure provides a pharmaceutical composition comprising the crystalline hydrochloride salt form IV as in any one of claims 64, 65, 66, 67, 68, 69, 70, 71, 72 or 73, or a mixture thereof, and a pharmaceutically acceptable excipient.

75. In another embodiment of the present disclosure, the present disclosure provides a method for preparing the crystalline hydrochloride salt form IV of claim 64, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, HCl, and a suitable solvent to form a crystalline hydrochloride salt form IV of Compound 1.

76. In another embodiment of the present disclosure, the present disclosure provides the method of claim 75 wherein the suitable solvent is MeCN or ethanol.

77. In another embodiment of the present disclosure, the present disclosure provides the method of claim 76, wherein the solvent is MeCN.

78. In another embodiment of the present disclosure, the present disclosure provides the method of claim 76, wherein the solvent is ethanol.

79. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline hydrochloride salt form IV of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

80. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 74.

81. In another embodiment of the present disclosure, the present disclosure provides the method of claim 80, wherein said disease mediated by KRAS G12C inhibition is cancer.

82. In another embodiment of the present disclosure, the present disclosure provides the method of claim 81, wherein the cancer is lung cancer, pancreatic cancer or colorectal cancer.

83. In another embodiment of the present disclosure, the present disclosure provides the method of claim 82, wherein the cancer is lung cancer.

84. In another embodiment of the present disclosure, the present disclosure provides the method of claim 82, wherein the lung cancer is non-small cell lung cancer.

85. In another embodiment of the present disclosure, the present disclosure provides a crystalline hydrochloride salt form V of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

86. In another embodiment of the present disclosure, the present disclosure provides the crystalline hydrochloride salt form V of Compound 1 of claim 85, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one is the M atropisomer.

Figure 13:
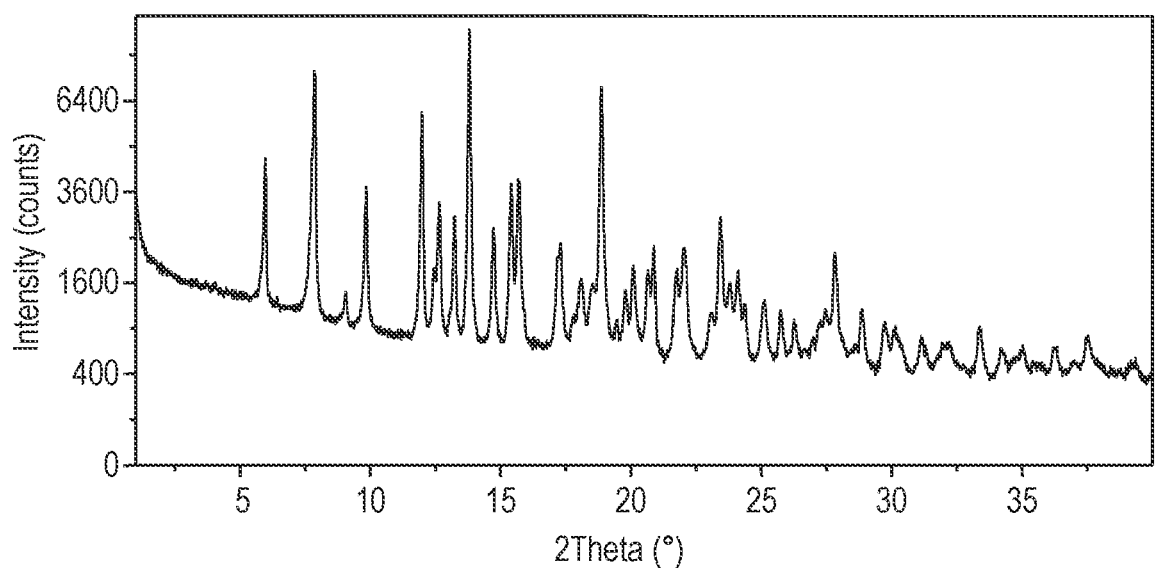
FIG. 13 shows XRPD data for the crystalline hydrochloride salt Form V of Compound 1.

87. In another embodiment of the present disclosure, the present disclosure provides the crystalline hydrochloride salt form V of claim 85, characterized by the powder X-ray diffraction pattern substantially as shown in FIG. 13.

88. In another embodiment of the present disclosure, the present disclosure provides the crystalline hydrochloride salt form V of Compound 1 of claim 85, wherein said form V is characterized by at least three peaks, at least five peaks, or at least seven peaks selected from a powder X-ray diffraction pattern comprising peaks at diffraction angle 2 theta degrees at approximately 6.0, 7.9, 9.1, 9.9, 12.0, 12.4, 12.7, 13.2, 13.8, 14.7, 15.4, 15.7, and 18.9.

89. In another embodiment of the present disclosure, the present disclosure provides the crystalline hydrochloride salt form V of Compound 1 of claim 85, wherein said form V is characterized by a powder X-ray diffraction pattern comprising peaks at diffraction angle 2 theta degrees at approximately 7.9, 9.9, 13.8 and 15.7.

90. In another embodiment of the present disclosure, the present disclosure provides the crystalline hydrochloride salt form V of Compound 1 of claim 85, having a differential scanning calorimetry thermogram comprising an endotherm with an onset of about 266° C.

91. In another embodiment of the present disclosure, the present disclosure provides the crystalline hydrochloride salt form V of Compound 1 of claim 85, having a thermogravimetric analysis thermogram comprising a weight loss of about 1.1% when heated from about 25° C. to about 200° C.

92. In another embodiment of the present disclosure, the present disclosure provides the crystalline hydrochloride salt form V of Compound 1 of claim 85, which is substantially pure.

93. In another embodiment of the present disclosure, the present disclosure provides a pharmaceutical composition comprising the crystalline hydrochloride salt form V of claim 85, and a pharmaceutically acceptable excipient.

94. In another embodiment of the present disclosure, the present disclosure provides a composition comprising an amorphous form of Compound 1 and the crystalline hydrochloride salt form V of Compound 1 of claim 85.

95. In another embodiment of the present disclosure, the present disclosure provides a pharmaceutical composition comprising the crystalline hydrochloride salt form V as in any one of claims 85, 86, 87, 88, 89, 90, 91, 92, 93 or 94 or a mixture thereof, and a pharmaceutically acceptable excipient.

96. In another embodiment of the present disclosure, the present disclosure provides the pharmaceutical composition of claim 95, wherein the composition is a single dose.

97. In another embodiment of the present disclosure, the present disclosure provides a method for preparing the crystalline hydrochloride salt form V of claim 85, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, HCl, and a suitable solvent to form a crystalline hydrochloride salt form V of Compound 1.

98. In another embodiment of the present disclosure, the present disclosure provides the method of claim 97 wherein the suitable solvent is acetone, isopropyl alcohol (IPA), ethanol, MeCN, MeOH or $Et_2O$.

99. In another embodiment of the present disclosure, the present disclosure provides the method of claim 98 wherein the suitable solvent is acetone.

100. In another embodiment of the present disclosure, the present disclosure provides the method of claim 98 wherein the suitable solvent is isopropyl alcohol.

101. In another embodiment of the present disclosure, the present disclosure provides the method of claim 98 wherein the suitable solvent is ethanol.

102. In another embodiment of the present disclosure, the present disclosure provides the method of claim 98 wherein the suitable solvent is MeCN.

103. In another embodiment of the present disclosure, the present disclosure provides the method of claim 98 wherein the suitable solvent is MeOH.

104. In another embodiment of the present disclosure, the present disclosure provides the method of claim 98 wherein the suitable solvent is $Et_2O$.

105. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline hydrochloride salt form V of claim 85.

106. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 95.

107. In another embodiment of the present disclosure, the present disclosure provides the method of claim 105, wherein said disease mediated by KRAS G12C inhibition is cancer.

108. In another embodiment of the present disclosure, the present disclosure provides the method of claim 107, wherein the cancer is lung cancer, pancreatic cancer or colorectal cancer.

109. In another embodiment of the present disclosure, the present disclosure provides the method of claim 107, wherein the cancer is lung cancer.

110. In another embodiment of the present disclosure, the present disclosure provides the method of claim 107, wherein the lung cancer is non-small cell lung cancer.

111. In another embodiment of the present disclosure, the present disclosure provides a crystalline hydrochloride salt form VI of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

112. In another embodiment of the present disclosure, the present disclosure provides the crystalline hydrochloride salt form VI of Compound 1 of claim 111, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one is the M atropisomer.

Figure 16:
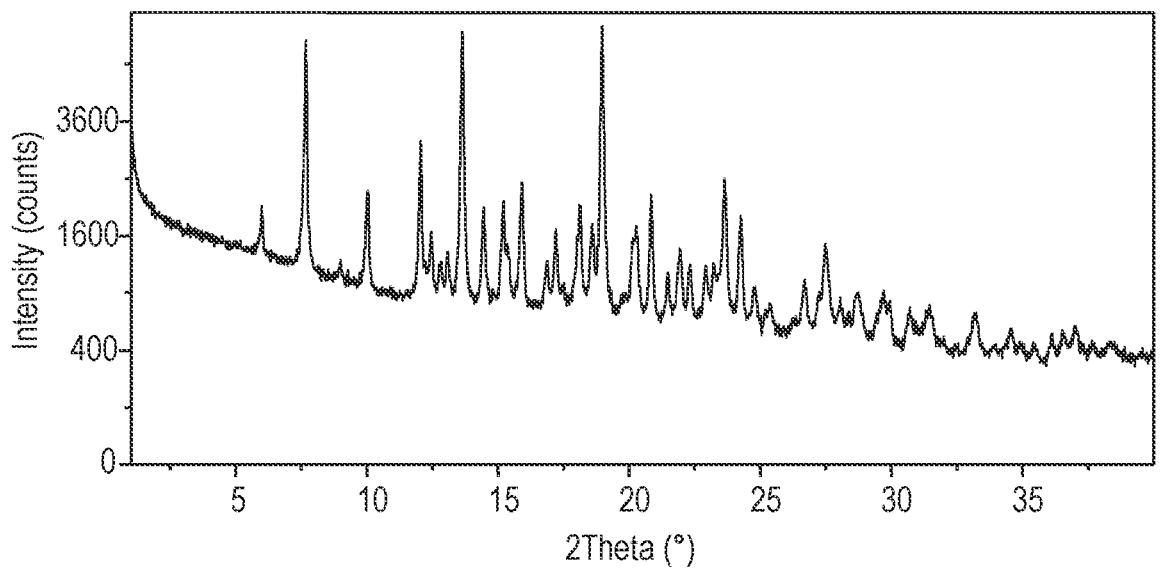
FIG. 16 shows XRPD data for the crystalline hydrochloride salt Form VI of Compound 1.

113. In another embodiment of the present disclosure, the present disclosure provides the crystalline hydrochloride salt form VI of claim 111, characterized by the powder X-ray diffraction pattern substantially as shown in FIG. 16.

114. In another embodiment of the present disclosure, the present disclosure provides the crystalline hydrochloride salt form VI of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one of claim 111, wherein said form VI is characterized by at least three peaks, at least five peaks, or at least seven peaks selected from a powder X-ray diffraction pattern comprising peaks at diffraction angle 2 theta degrees at approximately 6.0, 7.7, 10.0, 12.1, 12.5, 13.7, 14.5, 15.2, 15.9, 18.1, 19.0, and 20.9.

115. In another embodiment of the present disclosure, the present disclosure provides the crystalline hydrochloride salt form VI of Compound 1 of claim 111, wherein said form VI is characterized by a powder X-ray diffraction pattern comprising peaks at diffraction angle 2 theta degrees at approximately 7.7, 10.0 and 15.9.

116. In another embodiment of the present disclosure, the present disclosure provides the crystalline hydrochloride salt form VI of Compound 1 of claim 111 having a differential scanning calorimetry thermogram comprising an endotherm with an onset of about 273° C.

117. In another embodiment of the present disclosure, the present disclosure provides the crystalline hydrochloride salt form VI of Compound 1 of claim 111, having a thermogravimetric analysis thermogram comprising a weight loss of about 4% when heated from about 25° C. to about 250° C.

118. In another embodiment of the present disclosure, the present disclosure provides the crystalline hydrochloride salt form VI of Compound 1 of claim 111, which is substantially pure.

119. In another embodiment of the present disclosure, the present disclosure provides a pharmaceutical composition comprising the crystalline hydrochloride salt form VI of Compound 1 of claim 111, and a pharmaceutically acceptable excipient.

120. In another embodiment of the present disclosure, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline hydrochloride salt form VI of Compound 1 of claim 111.

121. In another embodiment of the present disclosure, the present disclosure provides a pharmaceutical composition comprising the crystalline hydrochloride salt form VI as in any one of claims 111, 112, 113, 114,115, 116, 117, 118, 119 or 120 or a mixture thereof, and a pharmaceutically acceptable excipient.

122. In another embodiment of the present disclosure, the present disclosure provides the pharmaceutical composition of claim 121, wherein the composition is a single dose.

123. In another embodiment of the present disclosure, the present disclosure provides a method for preparing the crystalline hydrochloride salt form VI of claim 111, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, HCl, and a suitable solvent to form a crystalline hydrochloride salt form VI of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

124. In another embodiment of the present disclosure, the present disclosure provides the method of claim 123 wherein the suitable solvent is p-dioxane.

125. In another embodiment of the present disclosure, the present disclosure provides the method of treating a disease mediated by KRAS G12C inhibition, the method comprising administering to a patient in need thereof a pharmaceutically effective amount of a pharmaceutical composition comprising the crystalline hydrochloride salt form VI of claim 111.

126. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 121.

127. In another embodiment of the present disclosure, the present disclosure provides the method of claim 126, wherein said disease mediated by KRAS G12C inhibition is cancer.

128. In another embodiment of the present disclosure, the present disclosure provides the method of claim 127, wherein the cancer is lung cancer, pancreatic cancer or colorectal cancer.

129 In another embodiment of the present disclosure, the present disclosure provides the method of claim 128, wherein the cancer is lung cancer.

130. In another embodiment of the present disclosure, the present disclosure provides the method of claim 129, wherein the lung cancer is non-small cell lung cancer.

131. In another embodiment of the present disclosure, the present disclosure provides a crystalline hydrochloride salt form VII of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

132. In another embodiment of the present disclosure, the present disclosure provides the crystalline hydrochloride salt form VII of Compound 1 of claim 131, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(11H)-one is the M atropisomer.

Figure 19:
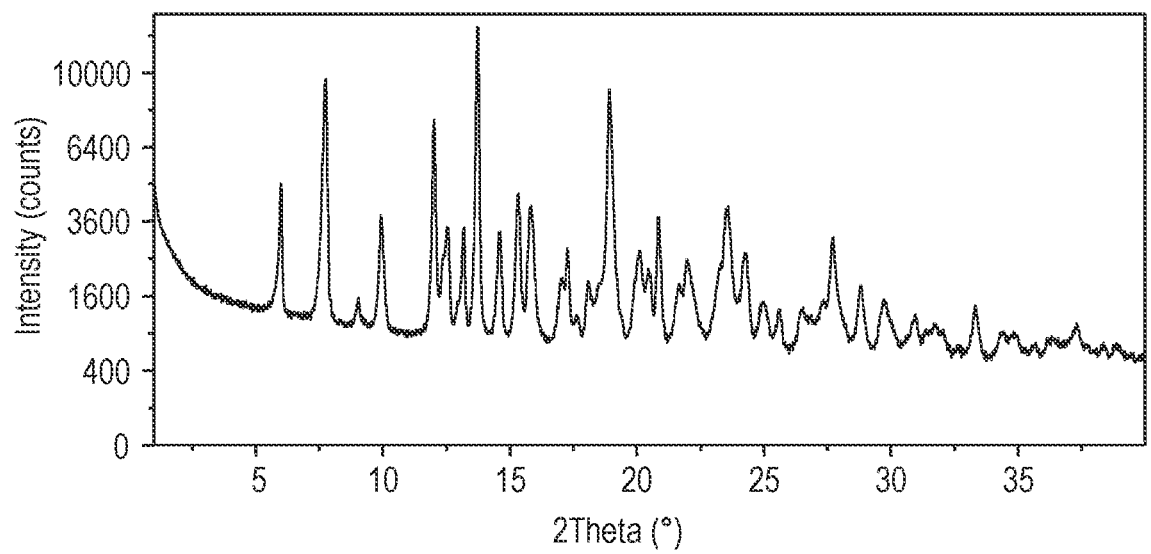
FIG. 19 shows XRPD data for the crystalline hydrochloride salt Form VII of Compound 1.

133. In another embodiment of the present disclosure, the present disclosure provides the crystalline hydrochloride salt form VII of claim 131, characterized by the powder X-ray diffraction pattern substantially as shown in FIG. 19.

134. In another embodiment of the present disclosure, the present disclosure provides the crystalline hydrochloride salt form VII of Compound 1 of claim 131, wherein said form VII is characterized by at least three peaks, at least five peaks, or at least seven peaks selected from a powder X-ray diffraction pattern comprising peaks at diffraction angle 2 theta degrees at approximately 6.0, 7.8, 9.0, 9.9, 12.0, 12.6, 13.2, 13.8, 14.6, 15.4, 15.8, 15.9, 18.9, 20.1, 20.6, and 20.9.

135. In another embodiment of the present disclosure, the present disclosure provides the crystalline hydrochloride salt form VII of Compound 1 of claim 131, wherein said form VII is characterized by a powder X-ray diffraction pattern comprising peaks at diffraction angle 2 theta degrees at approximately 7.8, 9.9, 13.2, and 14.6.

136. In another embodiment of the present disclosure, the present disclosure provides the crystalline hydrochloride salt form VII of Compound 1 of claim 131, having a differential scanning calorimetry thermogram comprising an endotherm with an onset of about 259° C.

137. In another embodiment of the present disclosure, the present disclosure provides the crystalline hydrochloride salt form VII of Compound 1 of claim 131, having a thermogravimetric analysis thermogram comprising an approximately negligible weight loss when heated from about 25° C. to about 250° C.

138. In another embodiment of the present disclosure, the present disclosure provides the crystalline hydrochloride salt form VII of Compound 1 of claim 131, which is substantially pure.

139. In another embodiment of the present disclosure, the present disclosure provides a pharmaceutical composition comprising the crystalline hydrochloride salt form VII of claim 131, and a pharmaceutically acceptable excipient.

140. In another embodiment of the present disclosure, the present disclosure provides a composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and the crystalline hydrochloride salt form VII of claim 131.

141. In another embodiment of the present disclosure, the present disclosure provides a pharmaceutical composition comprising the crystalline hydrochloride salt form VII as in any one of claims 131, 132, 133, 134, 135, 136, 137, 138, 139 or 140, or a mixture thereof, and a pharmaceutically acceptable excipient.

142. In another embodiment of the present disclosure, the present disclosure provides the pharmaceutical composition of claim 141, wherein the composition is a single dose.

143. In another embodiment of the present disclosure, the present disclosure provides a method for preparing the crystalline hydrochloride salt form VII of claim 131, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, HCl, and a suitable solvent to form a crystalline hydrochloride salt form VII of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

144. In another embodiment of the present disclosure, the present disclosure provides the method of claim 143 wherein the suitable solvent is ethanol.

145. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline hydrochloride salt form VII of claim 131.

146. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 141.

147. In another embodiment of the present disclosure, the present disclosure provides the method of claim 145, wherein said disease mediated by KRAS G12C inhibition is cancer.

148. In another embodiment of the present disclosure, the present disclosure provides the method of claim 147, wherein the cancer is lung cancer, pancreatic cancer or colorectal cancer.

149. In another embodiment of the present disclosure, the present disclosure provides the method of claim 148, wherein the cancer is lung cancer.

150. In another embodiment of the present disclosure, the present disclosure provides the method of claim 149, wherein the lung cancer is non-small cell lung cancer.

151. In another embodiment of the present disclosure, the present disclosure provides a crystalline phosphate salt form I of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

152. In another embodiment of the present disclosure, the present disclosure provides the crystalline phosphate salt form I of Compound 1 of claim 151, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one is the M atropisomer.

Figure 22:
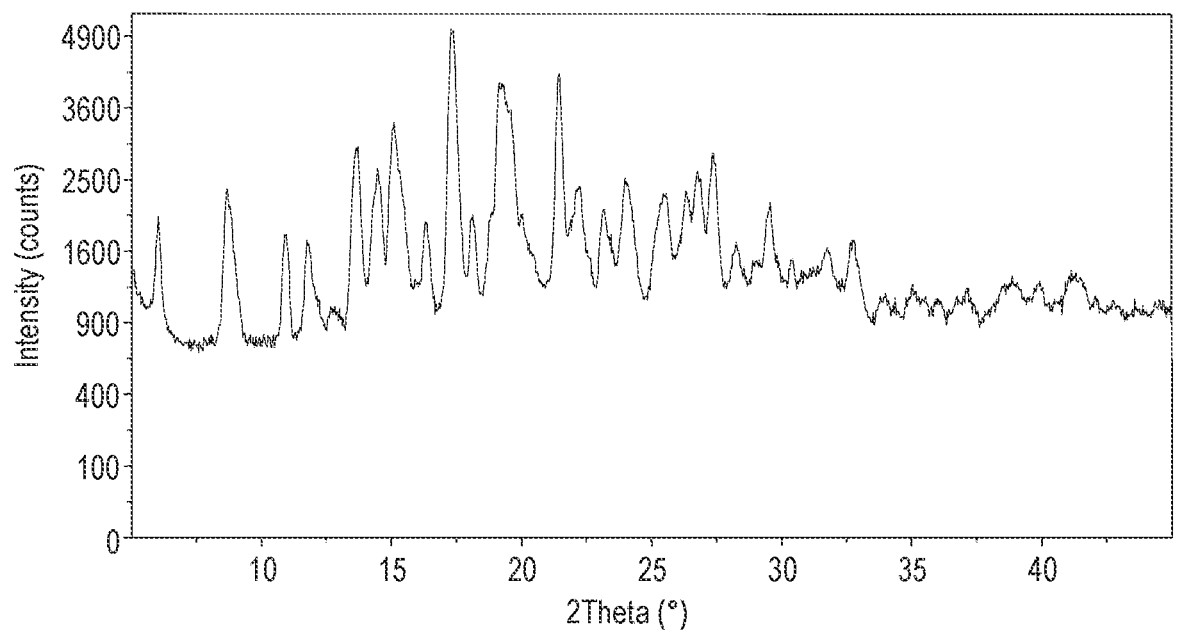
FIG. 22 shows XRPD data for the crystalline phosphate salt Form I of Compound 1.

153. In another embodiment of the present disclosure, the present disclosure provides the crystalline phosphate salt form I of claim 151, characterized by the powder X-ray diffraction pattern substantially as shown in FIG. 22.

154. In another embodiment of the present disclosure, the present disclosure provides the crystalline phosphate salt form I of Compound 1 of claim 151, wherein said phosphate salt form is characterized by at least three peaks, at least five peaks, or at least seven peaks selected from a powder X-ray diffraction pattern comprising peaks at diffraction angle 2 theta degrees at approximately 6.0, 8.7, 10.9, 11.8, 13.7, 14.5, 15.1, 17.2, 19.1, 19.6, 21.4, 24.0, 25.6, 26.3, 26.7, and 27.4.

155. In another embodiment of the present disclosure, the present disclosure provides the crystalline phosphate salt form I of Compound 1 of claim 151, wherein said phosphate salt form is characterized by a powder X-ray diffraction pattern comprising peaks at diffraction angle 2 theta degrees at approximately 8.7, 13.7, 14.5, 17.2 and 19.1.

156. In another embodiment of the present disclosure, the present disclosure provides the crystalline phosphate salt form I of Compound 1 of claim 151 having a differential scanning calorimetry thermogram comprising an endotherm with an onset of about 217° C.

157. In another embodiment of the present disclosure, the present disclosure provides the crystalline phosphate salt form I of Compound 1 of claim 151 having a thermogravimetric analysis thermogram comprising a weight loss of about 2.5% when heated from about 25° C. to about 200° C.

158. In another embodiment of the present disclosure, the present disclosure provides the crystalline phosphate salt form I of Compound 1 of claim 151, which is substantially pure.

159. In another embodiment of the present disclosure, the present disclosure provides a pharmaceutical composition comprising the crystalline phosphate salt form I of claim 151, and a pharmaceutically acceptable excipient.

160. In another embodiment of the present disclosure, the present disclosure provides a composition comprising an amorphous form of Compound 1 and the crystalline phosphate salt form I of claim 151.

161. In another embodiment of the present disclosure, the present disclosure provides a pharmaceutical composition comprising the crystalline phosphate salt form I as in any one of claims 151, 152, 153, 154, 155, 156, 157, 158, 159 or 160, or a mixture thereof, and a pharmaceutically acceptable excipient.

162. In another embodiment of the present disclosure, the present disclosure provides the pharmaceutical composition of claim 161, wherein the composition is a single dose.

163. In another embodiment of the present disclosure, the present disclosure provides a method for preparing the crystalline phosphate salt form I of claim 151, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, $H_3PO_4$, and a suitable solvent to form a crystalline phosphate salt form I of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

164. In another embodiment of the present disclosure, the present disclosure provides the method of claim 163 wherein the suitable solvent is methyl ethyl ketone (MEK).

165. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline phosphate salt form I of claim 151.

166. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 161.

168. In another embodiment of the present disclosure, the present disclosure provides the method of claim 165, wherein said disease mediated by KRAS G12C inhibition is cancer.

169. In another embodiment of the present disclosure, the present disclosure provides the method of claim 167, wherein the cancer is lung cancer, pancreatic cancer or colorectal cancer.

170. In another embodiment of the present disclosure, the present disclosure provides the method of claim 168, wherein the cancer is lung cancer.

171. In another embodiment of the present disclosure, the present disclosure provides the method of claim 169, wherein the lung cancer is non-small cell lung cancer.

172. In another embodiment of the present disclosure, the present disclosure provides a crystalline mesylate salt form I of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1).

173. In another embodiment of the present disclosure, the present disclosure provides the crystalline mesylate salt form I of Compound 1 of claim 171, wherein the 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one is the M atropisomer.

Figure 25:
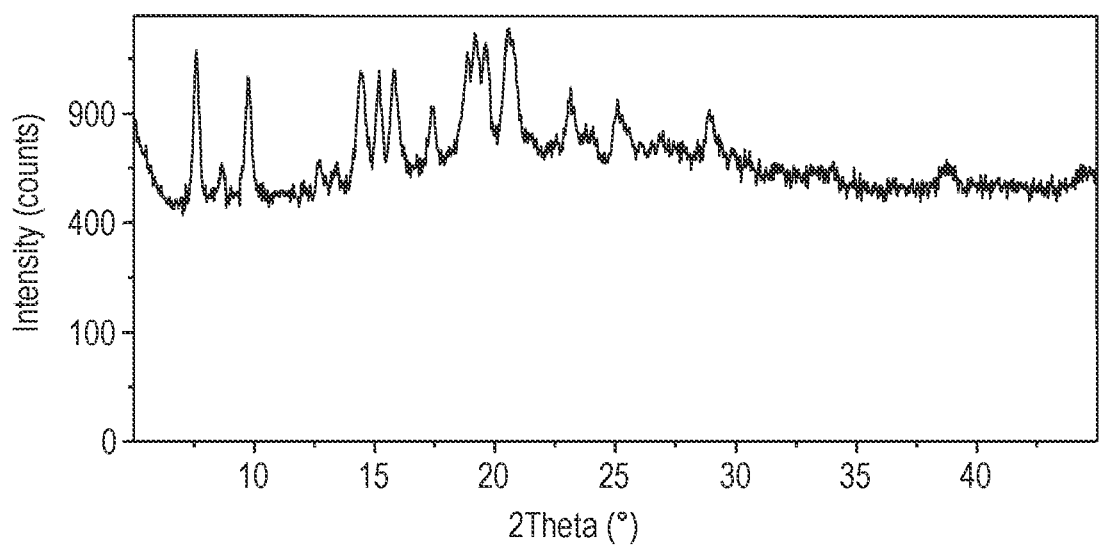
FIG. 25 shows XRPD data for the crystalline mesylate salt Form I of Compound 1.

174. In another embodiment of the present disclosure, the present disclosure provides the crystalline mesylate salt form I of claim 171, characterized by the powder X-ray diffraction pattern substantially as shown in FIG. 25.

175. In another embodiment of the present disclosure, the present disclosure provides the crystalline mesylate salt form I of Compound 1 of claim 171, wherein said mesylate salt form is characterized by at least three peaks, at least five peaks, or at least seven peaks selected from a powder X-ray diffraction pattern comprising peaks at diffraction angle 2 theta degrees at approximately 7.6, 8.7, 9.8, 14.6, 15.2, 15.8, 19.0, 19.6, 20.5, and 23.1.

176. In another embodiment of the present disclosure, the present disclosure provides the crystalline mesylate salt form I of Compound 1 of claim 171, wherein said mesylate salt form is characterized by a powder X-ray diffraction pattern comprising peaks at diffraction angle 2 theta degrees at approximately 7.6, 9.8, 15.8, 19.6 and 20.5.

177. In another embodiment of the present disclosure, the present disclosure provides the crystalline mesylate salt form I of Compound 1 of claim 171 having a differential scanning calorimetry thermogram comprising an endotherm with an onset of about 242° C.

178. In another embodiment of the present disclosure, the present disclosure provides the crystalline mesylate salt form I of Compound 1 of claim 171 having a thermogravimetric analysis thermogram comprising a weight loss of about 0.8% when heated from about 25° C. to about 200° C.

179. In another embodiment of the present disclosure, the present disclosure provides the crystalline mesylate salt form I of Compound 1 of claim 171 which is substantially pure.

180. In another embodiment of the present disclosure, the present disclosure provides a pharmaceutical composition comprising the crystalline mesylate salt form I of claim 171 and a pharmaceutically acceptable excipient.

181. In another embodiment of the present disclosure, the present disclosure provides a composition comprising an amorphous form of Compound 1 and the crystalline mesylate salt form I of claim 171.

182. In another embodiment of the present disclosure, the present disclosure provides a pharmaceutical composition comprising the crystalline mesylate salt form I as in any one of claims 171, 172, 173, 174, 175, 176, 177, 178, 179 or 180, or a mixture thereof, and a pharmaceutically acceptable excipient.

183. In another embodiment of the present disclosure, the present disclosure provides the pharmaceutical composition of claim 181, wherein the composition is a single dose.

184. In another embodiment of the present disclosure, the present disclosure provides a method for preparing the crystalline mesylate salt form I of claim 171, the method comprising: combining 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one, methanesulfonic acid, and a suitable solvent to form a crystalline mesylate salt form I of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

185. In another embodiment of the present disclosure, the present disclosure provides the method of claim 183 wherein the suitable solvent is ethyl acetate.

186. In another embodiment of the present disclosure, the present disclosure provides a method of treating a disease mediated by KRAS G12C inhibition, the method comprising administering to a patient in need thereof a pharmaceutically effective amount of a pharmaceutical composition comprising the crystalline mesylate salt form I of claim 171.

187. In another embodiment of the present disclosure, the present disclosure provides a method of treating a disease mediated by KRAS G12C inhibition, the method comprising administering to a patient in need thereof a pharmaceutically effective amount of a pharmaceutical composition of claim 181.

188. In another embodiment of the present disclosure, the present disclosure provides the method of claim 185, wherein said disease mediated by KRAS G12C inhibition is cancer.

189. In another embodiment of the present disclosure, the present disclosure provides the method of claim 187, wherein the cancer is lung cancer, pancreatic cancer or colorectal cancer.

190. In another embodiment of the present disclosure, the present disclosure provides the method of claim 188, wherein the cancer is lung cancer.

191. In another embodiment of the present disclosure, the present disclosure provides the method of claim 189, wherein the lung cancer is non-small cell lung cancer.

192. In another embodiment of the present disclosure, the present disclosure provides a pharmaceutical composition comprising an amorphous form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one and at least one crystalline form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one of claims 1, 20, 40, 64, 85, 111, 131, 151 or 171 and a pharmaceutically acceptable excipient.

193. In another embodiment of the present disclosure, the present disclosure provides the composition of claim 191, which comprises greater than about 50 weight percent crystalline 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one.

194. In another embodiment of the present disclosure, the present disclosure provides a pharmaceutical composition comprising at least one crystalline form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one of claims 1, 20, 40, 64, 85, 111, 131, 151 or 171 and a pharmaceutically acceptable excipient.

Alternative Embodiments

Provided herein as Embodiment 1 is a compound, wherein the compound is a crystalline hydrochloride salt form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1) or an atropisomer thereof.

Provided herein as Embodiment 2 is the compound of Embodiment 1, wherein the compound is the M atropisomer.

Provided herein as Embodiment 3 is the compound of Embodiment 1 or Embodiment 2, wherein the compound is characterized by the powder X-ray diffraction pattern substantially as shown in FIG. 1.

Provided herein as Embodiment 4 is the compound of Embodiment 1 or Embodiment 2, wherein the compound is characterized by at least three peaks, at least five peaks, or at least seven peaks selected from a powder X-ray diffraction pattern comprising peaks at diffraction angle 2 theta degrees at 6.6, 8.9, 10.9, 13.7, 14.2, 15.1, 18.0, 19.0, and 21.1±0.2 degrees 2 theta as measured by x-ray powder diffraction using an x-ray wavelength of 1.54 Å.

Provided herein as Embodiment 5 is the compound of Embodiment 1 or Embodiment 2, wherein the compound is characterized by a powder X-ray diffraction pattern comprising peaks at diffraction angle 2 theta degrees at 8.9, 10.9, and 14.2±0.2 degrees 2 theta as measured by x-ray powder diffraction using an x-ray wavelength of 1.54 Å.

Provided herein as Embodiment 6 is the compound of Embodiment 1 or Embodiment 2, wherein the compound is characterized by the powder X-ray diffraction pattern substantially as shown in FIG. 4.

Provided herein as Embodiment 7 is the compound of Embodiment 1 or Embodiment 2, wherein the compound is characterized by at least three peaks, at least five peaks, or at least seven peaks selected from a powder X-ray diffraction pattern comprising peaks at diffraction angle 2 theta degrees at 6.0, 6.3, 8.2, 10.6, 11.2, 12.7, 13.6, 14.3, 16.1, 16.5, 17.2, 21.6, and 21.4±0.2 degrees 2 theta as measured by x-ray powder diffraction using an x-ray wavelength of 1.54 Å.

Provided herein as Embodiment 8 is the compound of Embodiment 1 or Embodiment 2, wherein the compound is characterized by a powder X-ray diffraction pattern comprising peaks at diffraction angle 2 theta degrees at 6.3, 8.2, 10.6, and 16.1±0.2 degrees 2 theta as measured by x-ray powder diffraction using an x-ray wavelength of 1.54 Å.

Provided herein as Embodiment 9 is the compound of Embodiment 1 or Embodiment 2, wherein the compound is characterized by the powder X-ray diffraction pattern substantially as shown in FIG. 7.

Provided herein as Embodiment 10 is the compound of Embodiment 1 or Embodiment 2, wherein the compound is characterized by at least three peaks, at least five peaks, or at least seven peaks selected from a powder X-ray diffraction pattern comprising peaks at diffraction angle 2 theta degrees at 6.4, 8.4, 11.0, 11.2, 12.7, 13.6, 13.9, 15.0, 15.6, 16.6, 16.7, 16.8, and 21.2±0.2 degrees 2 theta as measured by x-ray powder diffraction using an x-ray wavelength of 1.54 Å.

Provided herein as Embodiment 11 is the compound of Embodiment 1 or Embodiment 2, wherein the compound is characterized by a powder X-ray diffraction pattern comprising peaks at diffraction angle 2 theta degrees at 6.4, 8.4, 11.0, and 15.6±0.2 degrees 2 theta as measured by x-ray powder diffraction using an x-ray wavelength of 1.54 Å.

Provided herein as Embodiment 12 is the compound of Embodiment 1 or Embodiment 2, wherein the compound is characterized by the powder X-ray diffraction pattern substantially as shown in FIG. 10.

Provided herein as Embodiment 13 is the compound of Embodiment 1 or Embodiment 2, wherein the compound is characterized by at least three peaks, at least five peaks, or at least seven peaks selected from a powder X-ray diffraction pattern comprising peaks at diffraction angle 2 theta degrees at 5.6, 6.5, 8.5, 11.3, 12.8, 13.6, 14.0, 14.1, 15.0, 16.7, 17.8, and 18.4±0.2 degrees 2 theta as measured by x-ray powder diffraction using an x-ray wavelength of 1.54 Å.

Provided herein as Embodiment 14 is the compound of Embodiment 1 or Embodiment 2, wherein the compound is characterized by a powder X-ray diffraction pattern comprising peaks at diffraction angle 2 theta degrees at 5.6, 6.5, and 8.5±0.2 degrees 2 theta as measured by x-ray powder diffraction using an x-ray wavelength of 1.54 Å.

Provided herein as Embodiment 15 is the compound of Embodiment 1 or Embodiment 2, wherein the compound is characterized by the powder X-ray diffraction pattern substantially as shown in FIG. 13.

Provided herein as Embodiment 16 is the compound of Embodiment 1 or Embodiment 2, wherein the compound is characterized by at least three peaks, at least five peaks, or at least seven peaks selected from a powder X-ray diffraction pattern comprising peaks at diffraction angle 2 theta degrees at 6.0, 7.9, 9.1, 9.9, 12.0, 12.4, 12.7, 13.2, 13.8, 14.7, 15.4, 15.7, and 18.9±0.2 degrees 2 theta as measured by x-ray powder diffraction using an x-ray wavelength of 1.54 Å.

Provided herein as Embodiment 17 is the compound of Embodiment 1 or Embodiment 2, wherein the compound is characterized by a powder X-ray diffraction pattern comprising peaks at diffraction angle 2 theta degrees at 7.9, 9.9, 13.8, and 15.7±0.2 degrees 2 theta as measured by x-ray powder diffraction using an x-ray wavelength of 1.54 Å.

Provided herein as Embodiment 18 is the compound of Embodiment 1 or Embodiment 2, wherein the compound is characterized by the powder X-ray diffraction pattern substantially as shown in FIG. 16.

Provided herein as Embodiment 19 is the compound of Embodiment 1 or Embodiment 2, wherein the compound is characterized by at least three peaks, at least five peaks, or at least seven peaks selected from a powder X-ray diffraction pattern comprising peaks at diffraction angle 2 theta degrees at 6.0, 7.7, 10.0, 12.1, 12.5, 13.7, 14.5, 15.2, 15.9, 18.1, 19.0, and 20.9±0.2 degrees 2 theta as measured by x-ray powder diffraction using an x-ray wavelength of 1.54 Å.

Provided herein as Embodiment 20 is the compound of Embodiment 1 or Embodiment 2, wherein the compound is characterized by a powder X-ray diffraction pattern comprising peaks at diffraction angle 2 theta degrees at 7.7, 10.0, and 15.9±0.2 degrees 2 theta as measured by x-ray powder diffraction using an x-ray wavelength of 1.54 Å.

Provided herein as Embodiment 21 is the compound of Embodiment 1 or Embodiment 2, wherein the compound is characterized by the powder X-ray diffraction pattern substantially as shown in FIG. 19.

Provided herein as Embodiment 22 is the compound of Embodiment 1 or Embodiment 2, wherein the compound is characterized by at least three peaks, at least five peaks, or at least seven peaks selected from a powder X-ray diffraction pattern comprising peaks at diffraction angle 2 theta degrees at 6.0, 7.8, 9.0, 9.9, 12.0, 12.6, 13.2, 13.8, 14.6, 15.4, 15.8, 15.9, 18.9, 20.1, 20.6, and 20.9±0.2 degrees 2 theta as measured by x-ray powder diffraction using an x-ray wavelength of 1.54 Å.

Provided herein as Embodiment 23 is the compound of Embodiment 1 or Embodiment 2, wherein the compound is characterized by a powder X-ray diffraction pattern comprising peaks at diffraction angle 2 theta degrees at 7.8, 9.9, 13.2, and 14.6±0.2 degrees 2 theta as measured by x-ray powder diffraction using an x-ray wavelength of 1.54 Å.

Provided herein as Embodiment 24 is a compound, wherein the compound is a crystalline phosphate salt form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(0H)-one (Compound 1) or an atropisomer thereof.

Provided herein as Embodiment 25 is the compound of Embodiment 24, wherein the compound is the M atropisomer.

Provided herein as Embodiment 26 is the compound of Embodiment 24 or Embodiment 25, wherein the compound is characterized by the powder X-ray diffraction pattern substantially as shown in FIG. 22.

Provided herein as Embodiment 27 is the compound of Embodiment 24 or Embodiment 25, wherein the compound is characterized by at least three peaks, at least five peaks, or at least seven peaks selected from a powder X-ray diffraction pattern comprising peaks at diffraction angle 2 theta degrees at 6.0, 8.7, 10.9, 11.8, 13.7, 14.5, 15.1, 17.2, 19.1, 19.6, 21.4, 24.0, 25.6, 26.3, 26.7, and 27.4±0.2 degrees 2 theta as measured by x-ray powder diffraction using an x-ray wavelength of 1.54 Å.

Provided herein as Embodiment 28 is the compound of Embodiment 24 or Embodiment 25, wherein the compound is characterized by a powder X-ray diffraction pattern comprising peaks at diffraction angle 2 theta degrees at 8.7, 13.7, 14.5, 17.2 and 19.1±0.2 degrees 2 theta as measured by x-ray powder diffraction using an x-ray wavelength of 1.54 Å.

Provided herein as Embodiment 29 is a compound, wherein the compound is a crystalline mesylate salt form of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1) or an atropisomer thereof.

Provided herein as Embodiment 30 is the compound of Embodiment 29, wherein the compound is the M atropisomer.

Provided herein as Embodiment 31 is the compound of Embodiment 29 or Embodiment 30, wherein the compound is characterized by the powder X-ray diffraction pattern substantially as shown in FIG. 25.

Provided herein as Embodiment 32 is the compound of Embodiment 29 or Embodiment 30, wherein the compound is characterized by at least three peaks, at least five peaks, or at least seven peaks selected from a powder X-ray diffraction pattern comprising peaks at diffraction angle 2 theta degrees at 7.6, 9.8, 14.6, 15.2, 15.8, 19.0, 19.6, 20.5, and 23.2±0.2 degrees 2 theta as measured by x-ray powder diffraction using an x-ray wavelength of 1.54 Å.

Provided herein as Embodiment 33 is the compound of Embodiment 29 or Embodiment 30, wherein the compound is characterized by a powder X-ray diffraction pattern comprising peaks at diffraction angle 2 theta degrees at 7.6, 9.8, 15.8, 19.6 and 20.5±0.2 degrees 2 theta as measured by x-ray powder diffraction using an x-ray wavelength of 1.54 Å.

Provided herein as Embodiment 34 is a pharmaceutical composition comprising the compound of any one of Embodiments 1-33 and a pharmaceutically acceptable excipient.

Provided herein as Embodiment 35 is a compound of any one of Embodiments 1-33 or the pharmaceutical composition of Embodiment 34 for use as a medicament.

Provided herein as Embodiment 36 is a compound of any one of Embodiments 1-33 or the pharmaceutical composition of Embodiment 34 for use in treating cancer having a KRAS G12C mutation.

Provided herein as Embodiment 37 is the compound or the pharmaceutical composition for use of Embodiment 36, wherein the cancer having a KRAS G12C mutation is lung cancer, pancreatic cancer, or colorectal cancer.

Provided herein as Embodiment 38 is the compound or the pharmaceutical composition for use of Embodiment 36, wherein the cancer having a KRAS G12C mutation is non-small cell lung cancer.

Provided herein as Embodiment 39 is the compound or the pharmaceutical composition for use of Embodiment 36, wherein the cancer having a KRAS G12C mutation is pancreatic cancer.

Provided herein as Embodiment 40 is the compound or the pharmaceutical composition for use of Embodiment 36, wherein the cancer having a KRAS G12C mutation is colorectal cancer.

Provided herein as Embodiment 41 is a use of the compound of any one of Embodiments 1-33 or the pharmaceutical composition of Embodiments 34 in the preparation of a medicament for treating cancer having a KRAS G12C mutation.

Provided herein as Embodiment 42 is the use of Embodiment 41, wherein the cancer having a KRAS G12C mutation is lung cancer, pancreatic cancer, or colorectal cancer.

Provided herein as Embodiment 43 is the use of Embodiment 41, wherein the cancer having a KRAS G12C mutation is non-small cell lung cancer.

Provided herein as Embodiment 44 is the use of Embodiment 41, wherein the cancer having a KRAS G12C mutation is pancreatic cancer.

Provided herein as Embodiment 45 is the use of Embodiment 41, wherein the cancer having a KRAS G12C mutation is colorectal cancer.

Provided herein as Embodiment 46 is a method of treating a cancer having a KRAS G12C mutation in a patient in need thereof, the method comprising administering to the patient a therapeutically effective amount of the compound of any one of Embodiments 1-33.

Provided herein as Embodiment 47 is the method of Embodiment 46, wherein the cancer having a KRAS G12C mutation is lung cancer, pancreatic cancer, or colorectal cancer.

Provided herein as Embodiment 48 is the method of Embodiment 46, wherein the cancer having a KRAS G12C mutation is small cell lung cancer.

Provided herein as Embodiment 49 is the method of Embodiment 46, wherein the cancer having a KRAS G12C mutation is pancreatic cancer.

Provided herein as Embodiment 50 is the method of Embodiment 46, wherein the cancer having a KRAS G12C mutation is colorectal cancer.

Crystallization Techniques
Anti-Solvent Precipitation

Solutions of the compounds of the disclosure were prepared in various solvents and an anti-solvent was then added. The solids that formed were isolated and analyzed.

Alternatively, solutions of the compounds of the disclosure were prepared in various solvents, an anti-solvent was then added and the samples were allowed to evaporate. The solids that formed were isolated and analyzed.

Alternatively, solutions of the compounds of the disclosure were prepared in various solvents, an anti-solvent was then added and the samples were cooled to 2° C. to 8° C. The solids that formed were isolated and analyzed.

Sonication

Solutions or suspensions of the compounds of the disclosure were prepared in various solvents and sonicated in an ice bath for 90-180 minutes. The solids were isolated and analyzed.

Slow Cool

Saturated solutions of the compounds of the disclosure were prepared in various solvents at either ambient or elevated temperature. Samples prepared at elevated temperature were allowed to cool to ambient or 2-8° C. The solids that formed were isolated and analyzed.

Evaporation

Solutions of the compounds of the disclosure were prepared in various solvents. Once complete dissolution was observed, the solvent was evaporated by vacuum at ambient or heated temperatures. The solids that formed were isolated and analyzed.

Slow Evaporation

Solutions of the compounds of the disclosure were prepared in various solvents. Once complete dissolution was observed, the solution was allowed to evaporate at ambient in a partially covered vial, with or without a blanket of nitrogen gas. The solids that formed were isolated and analyzed.

Alternatively, solutions of the compounds of the disclosure were prepared followed by sonication for about 90 minutes. Following sonication the samples were allowed to evaporate. Experiments that yielded glasses, were reworked by slurrying the materials with a 15 fold addition of anti-solvent (hexane at 50° C. or water at room temperature). Any resulting solids were isolated and analyzed.

Stress Experiments

Solutions or suspensions of the compounds of the disclosure were prepared in various solvents followed by sonication for 60 minutes. Samples were then stirred to 30° C. for 24-72 hours, followed by stirring at 50° C. for 24 hours. Samples were analyzed by XRPD at each stage before final isolation and analysis.

Slurry Experiments

Solutions of the compounds of the disclosure were prepared by adding enough solids to a given solvent so that excess solids were present. All forms described below can be obtained from various solvents, including, but not limited, to the specific solvents described in the Examples. The mixture was then agitated in a sealed vial at either ambient or elevated temperature. After a given amount of time, the solids were isolated by vacuum or centrifuge filtration and analyzed.

Analytical Techniques
X-Ray Powder Diffraction (XRPD)

X-ray powder diffraction data was obtained using the Phillips X-ray automated powder diffractometer (X'Pert) that was equipped with a fixed slit and a real time multi strip (RTMS) detector. The radiation was CuKα (1.54 Å) and the voltage and current were 45 kV and 40 mA, respectively. Data were collected at room temperature from 3.0 to 40.0 degree 2-theta; step size was 0.0167 degrees; counting time was 15.240 seconds. The stage was rotated at a revolution time of 1.0 second.

Alternatively, X-ray powder diffraction data was obtained using the PANalytical Empyrean automated powder diffractometer that was equipped with a soller slit, beam stop, short antiscatter extension, antiscatter knife edge and a scanning position-sensitive detector (X'Celerator). The radiation was CuKα (1.54 Å). A specimen of the sample was sandwiched between 3 um thick films and analyzed in transmission geometry.

Alternatively, X-ray powder diffraction data was obtained using the PANalytical X'Pert PRO X-ray diffraction system that was equipped with a programmable divergence slit and a real time multi strip (RTMS) detector. The radiation was CuKα (1.54 Å) and the voltage and current were 45 kV and 40 mA, respectively. Data were collected at room temperature from 3.0 to 30.0 or 5 to 45 degrees 2-theta; step size was 0.0334 degrees. The stage was rotated at a revolution time of 2.0 seconds.

It is noted that peak shift of about +/−0.2 degrees can occur in XRPD patterns and could be caused by factors such as sample preparation and instrument alignment.

Thermogravimetric Analysis (TGA)

Thermogravimetric analysis was performed on a TGA Discovery Series, TA Instruments. Samples were analyzed under nitrogen at heating rates of 10° C./min over a temperature range from 25° C. to 325° C.

Differential Scanning Calorimetry (DSC)

Differential scanning calorimetry data was collected using standard DSC mode (Discovery Series, TA Instruments). A heating rate of 10° C./min was employed over a temperature range from 25° C. to 350° C. Analysis was run under nitrogen and samples were loaded in aluminum pans. Indium was used as a calibration standard.

EXAMPLES

Example 1: Identification of Solid State Forms of Compound 1

Within the pharmaceutical research and development field, the investigation of a suitable solid-state form represents a crucial step. Investigating a solid-state form comprises several decisions, mainly the investigation of an anhydrous, salt or co-crystal form and the investigation of a polymorph of the respective anhydrous, salt or co-crystal. During a lead optimization program, several properties of research compounds are optimized, typically leading to one or a few candidates that continue into exploratory development programs. Typically, in the assessment and optimization of physical chemical parameters during lead optimization, the main focus is on solubility. In the present case, Compound 1 has good solubility features. Beyond the optimization of solubility, further physical chemical parameters, such as (1) melting point, (2) thermal behavior, (3) hygroscopicity, (4) crystal habit, (5) polymorphic behavior or physical stability, (6) impurity profile, and (7) chemical stability of the anhydrous or salt form, must be borne in mind when investigating the salt. The melting point of a drug, either as a free base, acid or salt form, should be higher than a certain threshold to allow processing steps such as drying or tableting. The assessment of thermal behavior, which is typically done by thermogravimetry (TGA) and differential scanning calorimetry (DSC), also includes solid-solid phase transitions. These may be either enantiotropic or monotropic and can be related to the conversion of one polymorph to another or one pseudo-polymorph to another pseudo-polymorph—e.g. a lower solvate or hydrate—or a true polymorph. Hygroscopicity plays a key role in the evaluation of solid-state forms, as this property is highly relevant for many process steps such as drying, storage, blending, granulation, to name but a few. Hygroscopicity can be investigated by dynamic vapor sorption (DVS). Basically this technique yields information on the amount of moisture that is taken up by the compound at a certain relative humidity level. Discussing thermal behavior and hygroscopicity represents the link to another parameter that has to be considered in anhydrous or salt investigation: a manageable polymorphic behavior is required for an anhydrous or salt form to continue in pharmaceutical development. Therefore, at least a brief assessment of polymorphism is typically carried out in an anhydrous or salt-investigation procedure. In this sense, a manageable polymorphic behavior is not equivalent to the existence of only one or two polymorphic forms, but rather to render a situation where the conversion of polymorphic forms that are not equivalent. Crystal habits can influence anhydrous or salt investigations, and optimization in many cases means moving away a drug in the form of needle-shaped crystals towards e.g. platelets or even cubic crystals exhibiting better flowability. Salt investigation can be a tool to improve impurity profiles of drugs since pharmaceutical salts often exhibit crystal structures that are quite different from the structure of the corresponding free base or acid.

Polymorph and Salt Screen

As a matter of convenience, "Compound 1" as referred to in the Examples that follow is to be understood to be the M atropisomer of Compound 1.

A polymorph and salt screen to generate the different solid forms of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (Compound 1) was carried out for each form as described below.

A number of hydrochloride salt Forms I, II, III, IV, V, VI, and VII of Compound 1 were investigated. Further characterization of these crystalline forms, such as melting point, thermal behavior, hygroscopicity, crystal habit, particle size, polymorphic behavior, stability, and purity, were investigated, including XRPD, TGA, and DSC analysis. Rel. Int % is the percent relative intensity based on the largest peak.

Figure 28:
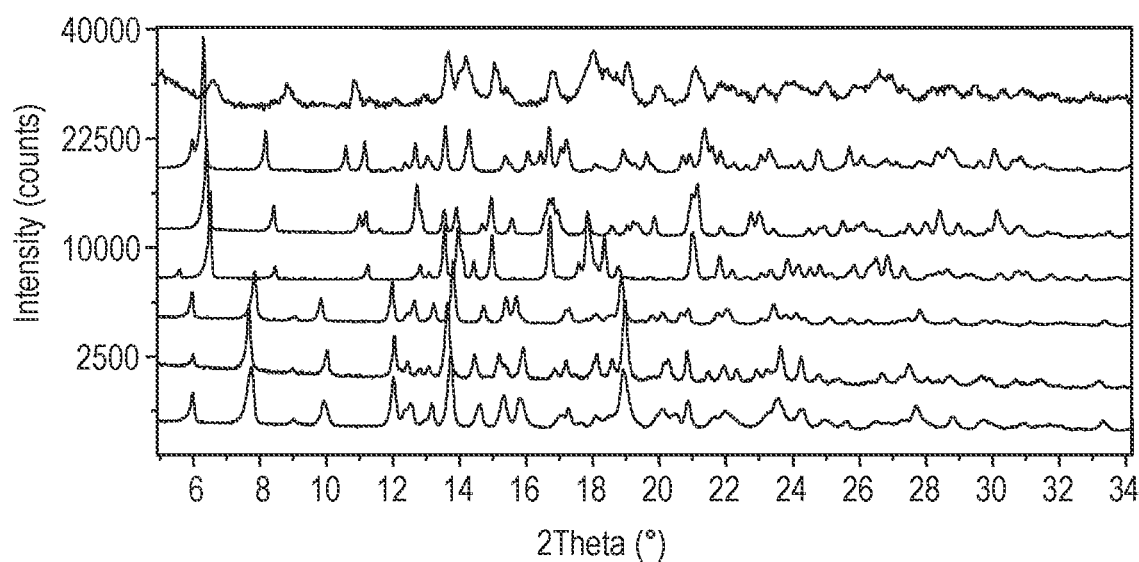
FIG. 28 shows the overlay of XRPD data of HCl Salts of Compound 1 (Forms I-VII top to bottom).

FIG. 28 illustrates the overlay of the XRPD data for the hydrochloride salt forms I, II, III, IV, V, VI, and VTI of Compound 1. Table A (below) illustrates the XRPD differentiating peaks for the Hydrochloride Salt Forms I-VII.

TABLE A

| XRPD Differentiating Peaks | | | | |
|---|---|---|---|---|
| HCl Salt Forms | Peaks Unique to Each Form (KA1°) | | | |
| Form I | 8.9 | 10.9 | 14.2 | |
| Form II | 6.3 | 8.2 | 10.6 | 16.1 |
| Form III | 6.4 | 8.4 | 11.0 | 15.6 |
| Form IV | 5.6 | 6.5 | 8.5 | |
| Form V | 7.9 | 9.9 | 13.8 | 15.7 |
| Form VI | 7.7 | 10.0 | 15.9 | |
| Form VII | 7.8 | 9.9 | 13.2 | 14.6 |

Example 1

The hydrochloride salt Form I of Compound 1, was prepared by charging Compound 1 (25 mg) with 3.71 uL HCl (1:1 mol/mol) and 1.25 mL EtOAc; then slurried at RT for 24 h.

Figure 2:
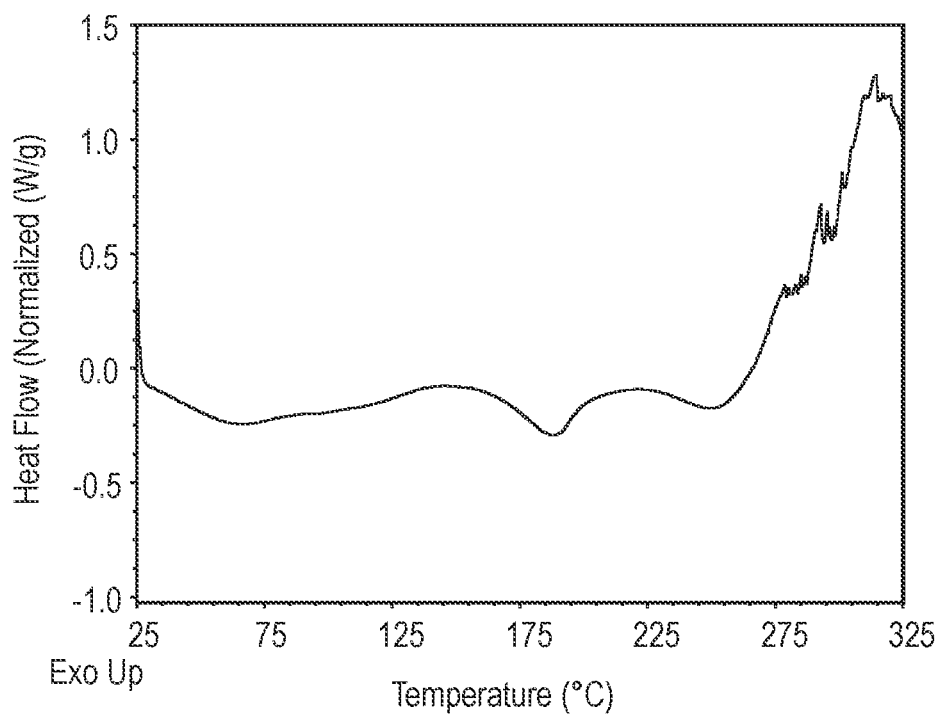
FIG. 2 shows DSC data for the hydrochloride salt Form I of Compound 1.
Figure 3:
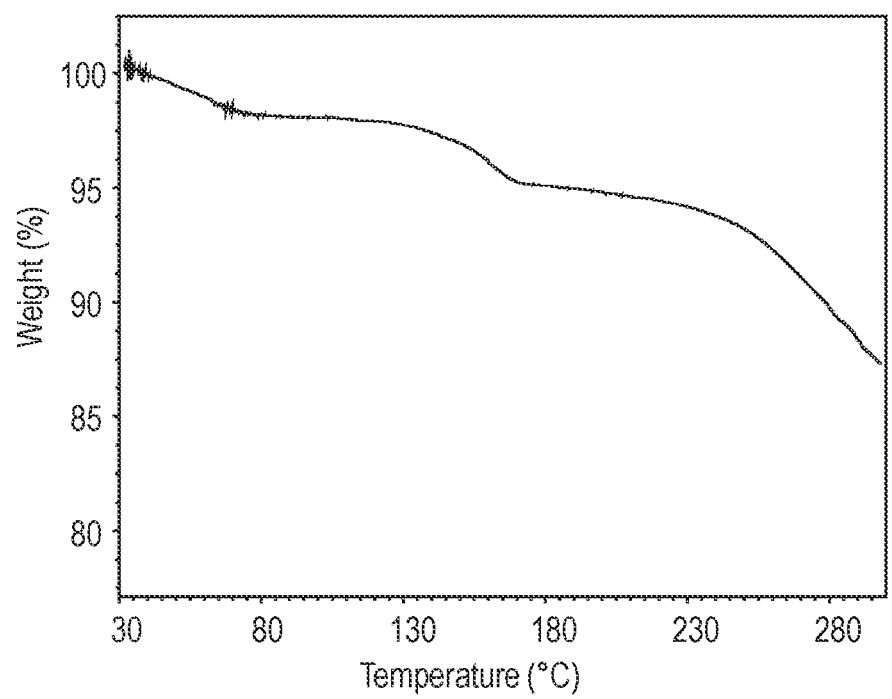
FIG. 3 shows TGA data for the hydrochloride salt Form I of Compound 1.

The relative peak areas of the hydrochloride form I of the XRPD, TGA, and DSC are represented in FIGS. 1, 2, and 3.

DSC onset of about 192° C., TGA comprising a weight loss of about 0.2% to about 5.3% when heated from about 30° C. to about 150° C.

NMR: $^1$H NMR (500 MHz, DMSO-$d_6$) δ ppm 0.97-1.13 (m, 4H) 1.13-1.28 (m, 4H) 1.35 (d, J=6.75 Hz, 3H) 1.95-2.01 (m, 1H) 2.07 (br s, 2H) 2.82-3.03 (m, 1H) 3.03-3.21 (m, 1H) 3.27 (br d, J=8.56 Hz, 1H) 3.36-3.58 (m, 1H) 3.59-3.71 (m, 1H) 3.94-4.09 (m, 2H) 4.15 (br d, J=12.46 Hz, 2H) 4.23-4.44 (m, 5H) 4.94 (br s, 2H) 5.69-5.82 (m, 2H) 6.10-6.27 (m, 2H) 6.64-6.79 (m, 3H) 6.79-6.96 (m, 2H) 7.18-7.36 (m, 2H) 7.62 (br s, 1H) 8.23-8.37 (m, 1H) 8.58 (br s, 1H) 9.07-9.29 (m, 1H) 9.37 (br s, 1H) 10.29 (br s, 1H)

TABLE 1

XRPD Peak Table

| Pos [°2Th.] | Rel. Int. [%] |
|---|---|
| 6.6 | 32.1 |
| 8.9 | 37.6 |
| 10.9 | 44.8 |
| 13.7 | 99.0 |
| 14.2 | 89.5 |
| 15.1 | 77.9 |
| 16.8 | 57.5 |
| 18.0 | 100.0 |
| 19.0 | 73.3 |
| 20.0 | 27.3 |
| 21.1 | 62.9 |
| 21.83 | 28.7 |
| 23.1 | 29.1 |
| 23.8 | 31.2 |
| 25.0 | 31.5 |
| 26.8 | 38.0 |
| 28.7 | 18.7 |
| 29.5 | 18.7 |
| 37.2 | 17.5 |
| 40.4 | 9.6 |

Example 2: Preparation of Crystalline Hydrochloride Salt Form II of Compound 1

Crystalline hydrochloride salt Form II was prepared by evaporation at ambient conditions from a concentrated solution of Compound 1 and HCl in MeOH. It was also prepared from slow cooling a concentrated solution of Compound 1 from 60 to 5° C. in 20:80 v/v MeOH/H$_2$O.

DSC onset: endotherms of about 114 and 203° C.

TGA: comprising a weight loss of about 9% when heated from about 20° C. to about 90° C.

Figure 5:
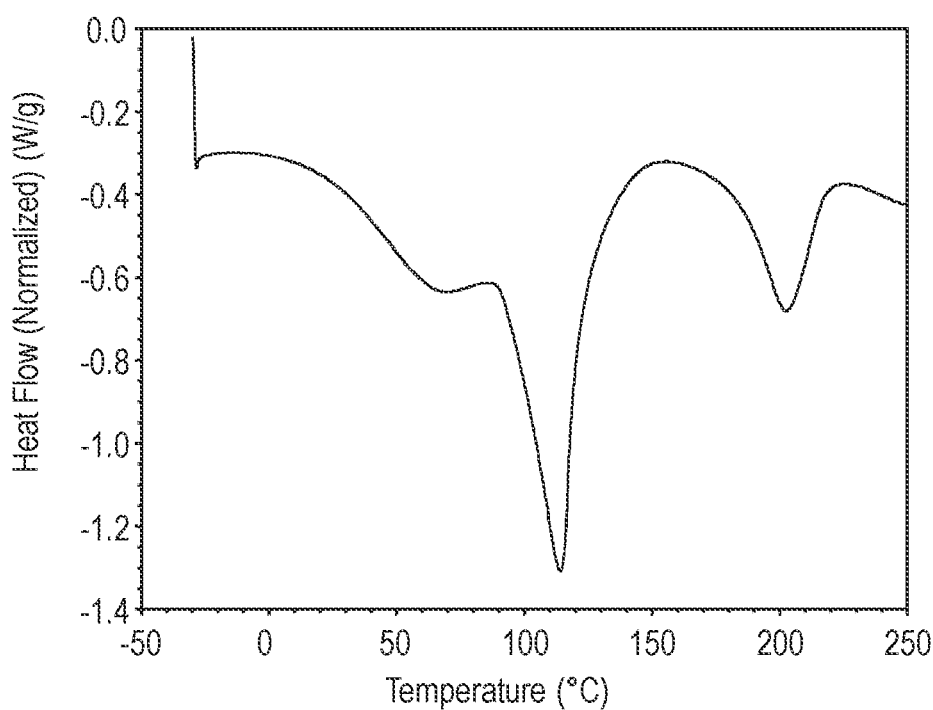
FIG. 5 shows DSC data for crystalline hydrochloride salt Form II of Compound 1.
Figure 6:
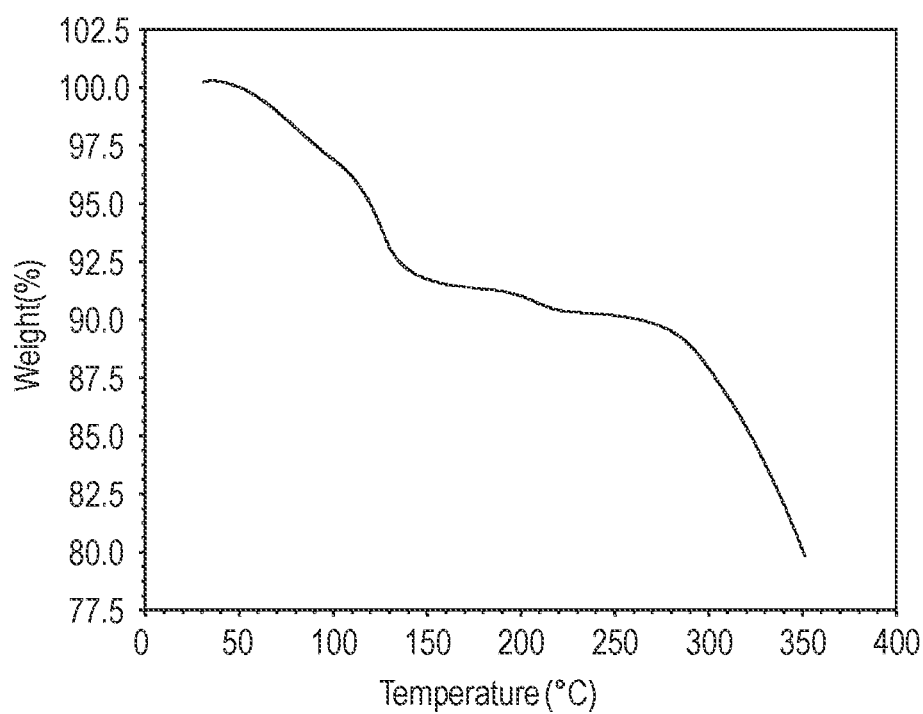
FIG. 6 shows TGA data for crystalline hydrochloride salt Form II of Compound 1.

The crystalline form of hydrochloride salt Form II prepared above was characterized by proton NMR, X-ray powder diffraction (XRPD) data (FIG. 4), DSC (FIG. 5), and TGA (FIG. 6).

NMR: $^1$H NMR (400 MHz, DMSO-6) δ ppm 1.00-1.11 (m, 2H) 1.11-1.29 (m, 3H) 1.35 (d, J=6.82 Hz, 2H) 2.00-2.17 (m, 2H) 2.94 (br s, 1H) 3.03-3.21 (m, 1H) 3.27 (br d, J=10.87 Hz, 1H) 3.52 (br d, J=13.00 Hz, 2H) 3.64 (br d, J=11.29 Hz, 3H) 3.90-4.09 (m, 4H) 4.09-4.22 (m, 2H) 4.23-4.45 (m, 5H) 4.94 (br s, 2H) 5.65-5.86 (m, 2H) 6.09-6.26 (m, 2H) 6.65-6.92 (m, 2H) 6.79-6.95 (m, 1H) 7.28 (td, J=8.20, 7.03 Hz, 2H) 7.65 (br s, 2H) 8.25-8.42 (m, 2H) 8.51-8.70 (m, 2H) 10.31 (br s, 1H).

TABLE 2

XRPD data of the Crystalline Hydrochloride salt Form II of Compound 1
XRPD Peak Table:

| Pos. [°2Th.] | Rel. Int. [%] |
|---|---|
| 3.0 | 4.6 |
| 6.0 | 19.1 |
| 6.3 | 100.0 |
| 8.2 | 26.3 |
| 9.0 | 0.9 |
| 10.6 | 16.2 |
| 11.2 | 19.2 |
| 12.0 | 2.4 |
| 12.4 | 5.4 |
| 12.7 | 18.4 |
| 13.0 | 9.2 |
| 13.6 | 30.9 |
| 14.3 | 27.5 |
| 15.4 | 9.9 |
| 16.1 | 12.8 |
| 16.5 | 12.4 |
| 16.7 | 29.5 |
| 17.1 | 15.4 |
| 17.2 | 20.6 |
| 18.1 | 4.5 |
| 18.9 | 13.9 |
| 19.3 | 5.3 |
| 19.6 | 12.3 |
| 20.7 | 10.4 |
| 20.9 | 11.5 |
| 21.4 | 29.3 |
| 21.6 | 17.1 |
| 21.9 | 12.9 |
| 22.3 | 5.7 |
| 22.6 | 3.4 |
| 23.1 | 10.7 |
| 23.3 | 14.8 |
| 24.0 | 4.2 |
| 24.2 | 7.0 |
| 24.8 | 13.6 |
| 25.7 | 16.1 |
| 26.1 | 10.0 |
| 26.8 | 8.2 |
| 27.2 | 6.2 |
| 27.8 | 6.4 |
| 28.3 | 12.6 |
| 28.6 | 14.9 |
| 29.3 | 4.0 |
| 29.6 | 7.5 |
| 30.1 | 15.0 |
| 30.6 | 6.6 |
| 30.9 | 9.9 |
| 31.5 | 5.1 |
| 32.2 | 1.8 |
| 32.6 | 2.4 |
| 33.2 | 2.2 |
| 34.2 | 4.5 |
| 35.1 | 1.5 |
| 36.5 | 2.6 |
| 37.2 | 1.6 |
| 38.0 | 1.9 |
| 38.3 | 1.8 |

Example 3: Preparation of the Hydrochloride Salt Form III (Trihydrate) of the Compound 1

The hydrochloride salt Form III of Compound 1 was prepared by drying hydrochloride salt Form I in RT under vacuum for 2 days. The hydrochloride salt Form III (trihydrate) of Compound 1 was also prepared by adding HCl to a concentrated solution of Compound 1 in dichloromethane precipitating out the HCl salt. The Hydrochloride Salt Form III (trihydrate) of Compound 1 was also prepared by evaporation at ambient conditions from a concentrated solution of Compound 1 and HCl in EtOH, 1:2 EtOH/H$_2$O. Further, the Hydrochloride Salt Form III (trihydrate) of Compound 1 was also prepared by crash precipitation from a solution of Compound 1 and HCl in 1-BuOH with the anti-solvent heptane.

DSC: endotherms about 129 and 213° C.; TGA: comprising a weight loss of about 8% when heated from about 20° C. to about 200° C.

Figure 8:
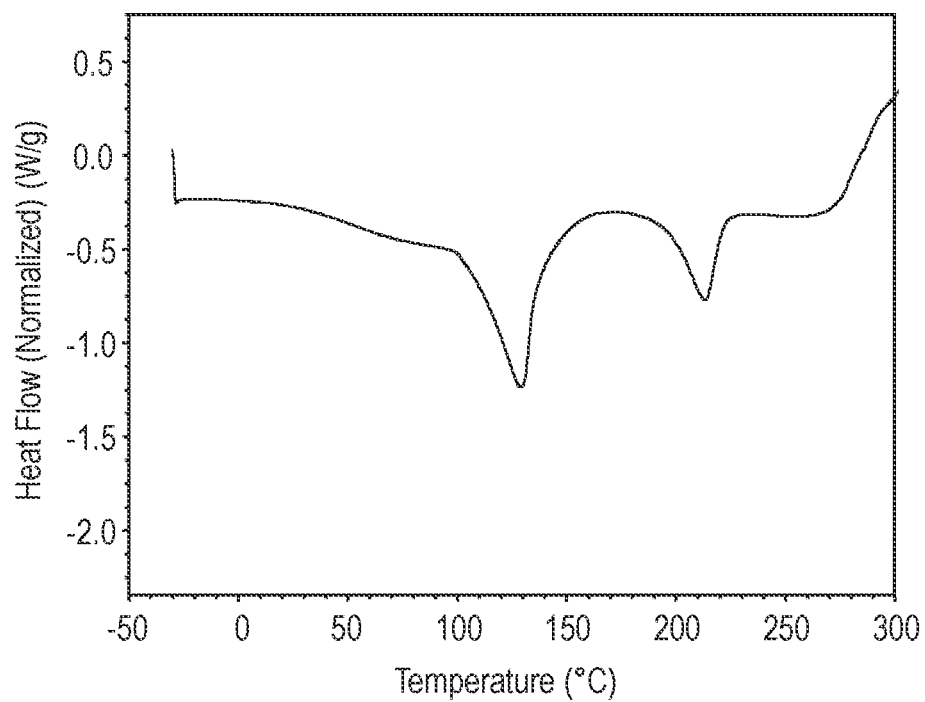
FIG. 8 shows DSC data for crystalline hydrochloride salt Form III of Compound 1.
Figure 9:
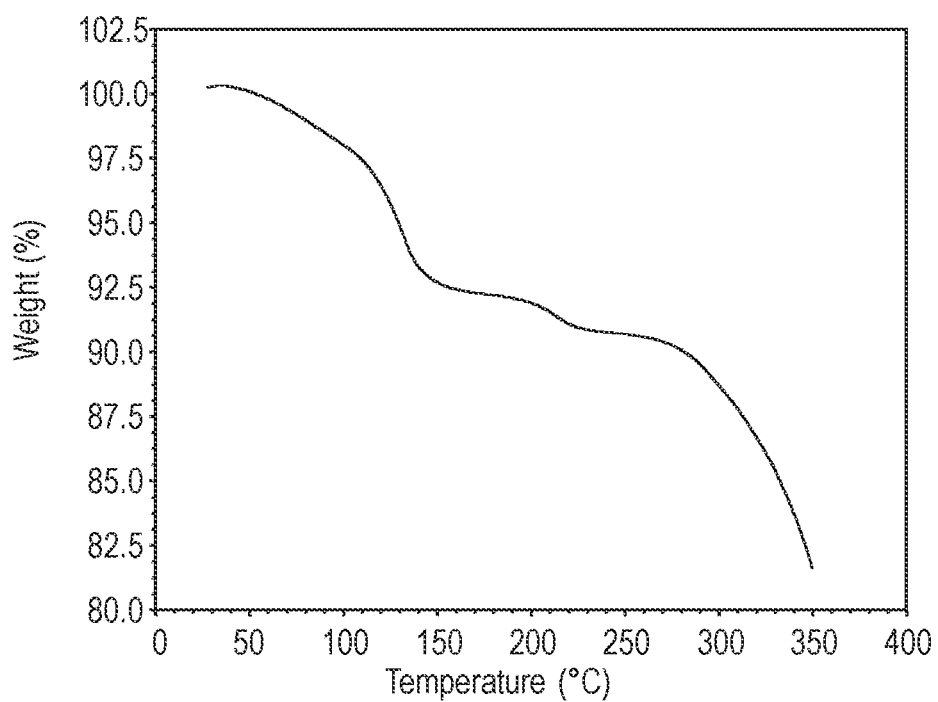
FIG. 9 shows TGA data for crystalline hydrochloride salt Form III of Compound 1.

The hydrochloride salt Form III of Compound 1 prepared above was characterized by proton NMR, X-ray powder diffraction (XRPD) data (FIG. 7), DSC (FIG. 8), and TGA (FIG. 9).

NMR: $^1$H NMR (400 MHz, DMSO-d$_6$) δ ppm 0.99-1.10 (m, 2H) 1.11-1.28 (m, 3H) 1.35 (d, J=6.82 Hz, 2H) 2.00-2.14

(m, 3H) 2.93 (br s, 2H) 3.03-3.21 (m, 1H) 3.27 (br d, J=10.23 Hz, 1H) 3.38-3.52 (m, 2H) 3.53-3.72 (m, 6H) 3.90-4.09 (m, 2H) 4.09-4.22 (m, 2H) 4.23-4.39 (m, 3H) 4.94 (br s, 3H) 5.65-5.87 (m, 2H) 6.06-6.35 (m, 2H) 6.59-6.79 (m, 3H) 6.86 (dt, J=16.30, 10.71 Hz, 1H) 7.28 (td, J=8.31, 7.03 Hz, 2H) 7.62 (br s, 1H) 8.23-8.42 (m, 2H) 8.50-8.70 (m, 2H) 10.29 (br s, 1H)

TABLE 3

XRPD data of the crystalline Hydrochloride Salt Form III of Compound I

| Pos. [°2Th.] | Rel. Int. [%] |
| --- | --- |
| 6.4 | 100.0 |
| 8.4 | 25.3 |
| 11.0 | 16.6 |
| 11.2 | 19.4 |
| 11.6 | 3.8 |
| 12.7 | 49.5 |
| 12.9 | 19.7 |
| 13.6 | 22.1 |
| 13.9 | 25.1 |
| 14.7 | 8.5 |
| 15.0 | 36.2 |
| 15.6 | 13.1 |
| 16.6 | 17.3 |
| 16.7 | 33.1 |
| 16.8 | 35.4 |
| 17.0 | 22.3 |
| 17.9 | 19.1 |
| 18.6 | 8.0 |
| 19.0 | 8.6 |
| 19.2 | 12.1 |
| 19.4 | 10.6 |
| 19.9 | 17.6 |
| 21.0 | 39.5 |
| 21.2 | 51.1 |
| 21.9 | 7.6 |
| 22.8 | 21.6 |
| 23.0 | 21.8 |
| 23.5 | 5.3 |
| 24.5 | 6.7 |
| 24.8 | 7.8 |
| 25.0 | 8.9 |
| 25.5 | 14.1 |
| 25.9 | 9.7 |
| 26.1 | 12.9 |
| 26.5 | 5.8 |
| 27.2 | 3.0 |
| 27.5 | 11.3 |
| 28.0 | 12.9 |
| 28.4 | 25.0 |
| 29.0 | 11.9 |
| 29.3 | 4.9 |
| 29.9 | 6.5 |
| 30.1 | 24.8 |
| 30.8 | 10.2 |
| 31.7 | 4.7 |
| 32.0 | 2.9 |
| 32.8 | 1.6 |
| 33.2 | 2.3 |
| 33.5 | 4.8 |
| 34.4 | 7.2 |
| 35.5 | 0.9 |
| 36.2 | 2.9 |
| 36.5 | 5.2 |
| 37.2 | 0.6 |
| 38.1 | 3.1 |
| 38.6 | 2.7 |
| 39.5 | 1.8 |

Example 4: Preparation of Hydrochloride Salt Form IV (Sesquihydrate) of Compound 1

The crystalline hydrochloride Salt Form IV of Compound 1 was prepared by adding HCl to a concentrated solution of Compound 1 in MeCN, and then precipitating out the HCl salt. The crystalline Hydrochloride Salt Form IV of Compound 1 was also prepared by evaporation at ambient conditions from a concentrated solution of Compound 1 and HCl in EtOH.

Figure 11:
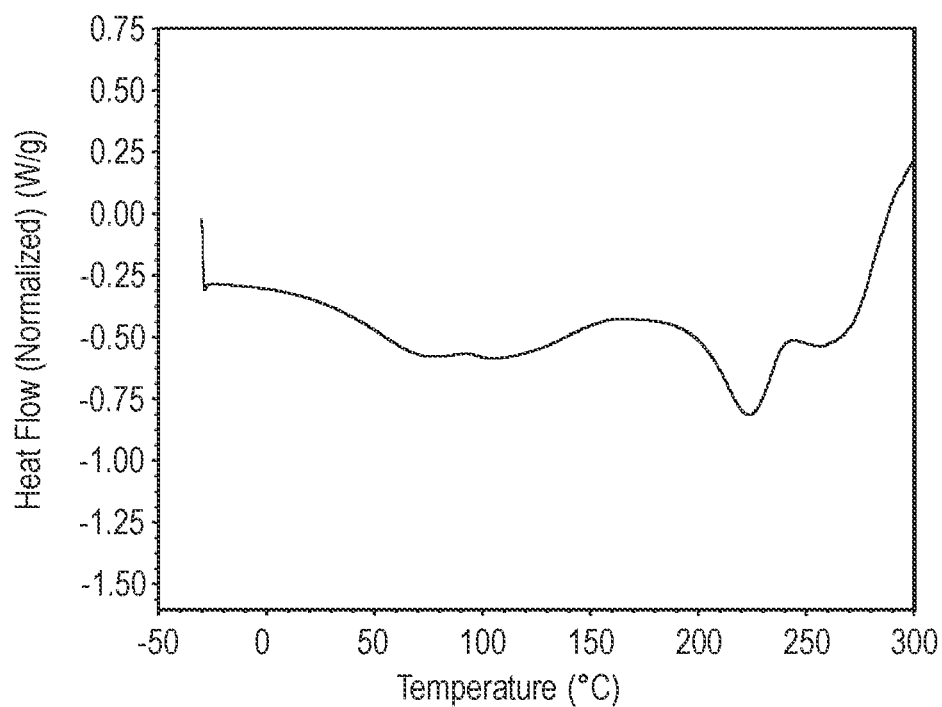
FIG. 11 shows DSC data for crystalline hydrochloride salt Form IV of Compound 1.
Figure 12:
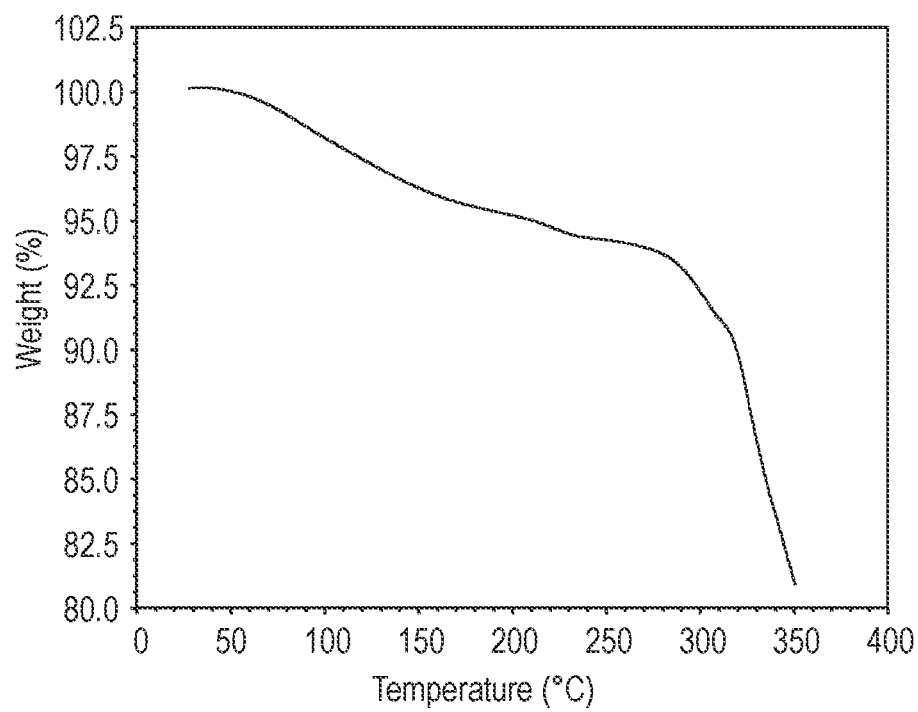
FIG. 12 shows TGA data for crystalline hydrochloride salt Form IV of Compound 1.

The crystalline form of hydrochloride salt Form IV prepared above was characterized by proton NMR, X-ray powder diffraction (XRPD) data (FIG. 10), DSC (FIG. 11), and TGA (FIG. 12).

DSC: endotherm of about 223° C.

TGA: comprising a weight loss of about 4.4% when heated from about 25° C. to about 95° C.

$^1$H NMR (400 MHz, DMSO-$d_6$) δ ppm 1.00-1.10 (m, 2H) 1.19 (br d, J=6.82 Hz, 2H) 1.35 (d, J=6.82 Hz, 2H) 2.07 (br d, J=1.70 Hz, 2H) 2.81-3.03 (m, 1H) 3.03-3.22 (m, 1H) 3.22-3.40 (m, 1H) 3.40-3.58 (m, 1H) 3.58-3.68 (m, 1H) 3.90-4.09 (m, 3H) 4.15 (br d, J=13.64 Hz, 1H) 4.23-4.39 (m, 2H) 4.94 (br s, 1H) 5.66-5.88 (m, 1H) 6.07-6.34 (m, 2H) 6.63-6.78 (m, 2H) 6.86 (dt, J=16.57, 10.68 Hz, 1H) 7.28 (td, J=8.31, 7.03 Hz, 1H) 7.62 (br s, 1H) 8.23-8.50 (m, 1H) 8.59 (br d, J=5.11 Hz, 1H) 10.29 (br s, 1H).

TABLE 4

XRPD data of the Hydrochloride Salt Form IV of Compound 1
XRPD Table

| Pos. [°2Th.] | Rel. Int. [%] |
| --- | --- |
| 5.6 | 9.41 |
| 6.5 | 100.00 |
| 8.5 | 12.35 |
| 11.3 | 13.96 |
| 12.8 | 14.15 |
| 13.1 | 6.74 |
| 13.6 | 58.37 |
| 14.0 | 56.95 |
| 14.1 | 26.37 |
| 14.5 | 18.60 |
| 15.0 | 47.59 |
| 16.7 | 71.58 |
| 17.6 | 17.73 |
| 17.8 | 77.00 |
| 18.4 | 47.19 |
| 18.8 | 13.68 |
| 19.7 | 2.34 |
| 20.3 | 1.82 |
| 21.0 | 51.28 |
| 21.8 | 24.91 |
| 22.2 | 9.56 |
| 22.6 | 3.02 |
| 23.1 | 6.80 |
| 23.4 | 10.22 |
| 23.9 | 21.28 |
| 24.2 | 15.33 |
| 24.5 | 12.56 |
| 24.8 | 15.74 |
| 25.2 | 6.57 |
| 25.8 | 15.38 |
| 26.3 | 11.42 |
| 26.5 | 23.60 |
| 26.8 | 24.31 |
| 27.3 | 13.42 |
| 28.0 | 4.51 |
| 28.4 | 8.18 |
| 28.6 | 11.12 |
| 29.2 | 5.54 |
| 29.4 | 5.89 |
| 30.2 | 5.83 |
| 30.7 | 8.17 |
| 30.8 | 8.95 |
| 31.0 | 8.89 |
| 31.8 | 6.22 |
| 32.3 | 3.08 |
| 32.8 | 5.32 |
| 33.2 | 1.65 |

TABLE 4-continued

XRPD data of the Hydrochloride Salt Form IV of Compound 1
XRPD Table

| Pos. [°2Th.] | Rel. Int. [%] |
| --- | --- |
| 33.8 | 3.60 |
| 34.2 | 3.14 |
| 34.7 | 4.00 |
| 36.2 | 4.95 |
| 36.5 | 5.84 |
| 37.1 | 6.90 |
| 38.0 | 1.09 |
| 38.5 | 2.67 |
| 39.4 | 1.30 |

Example 5: Preparation of Hydrochloride Salt Form V of Compound 1

The crystalline form of the hydrochloride salt Form V was prepared by slurry of Compound 1 and HCl in acetone or IPA. The crystalline form of the hydrochloride salt Form V was also prepared by evaporation at ambient conditions from a concentrated solution of Compound 1 and HCl in EtOH. The crystalline form of the hydrochloride salt Form V was also prepared by crash precipitation from a solution of Compound 1 and HCl in MeCN or MeOH with the anti-solvent $Et_2O$.

DSC: endotherm of about 266° C.

TGA: comprising a weight loss of about 1.1% when heated from about 25° C. to about 200° C.

Figure 14:
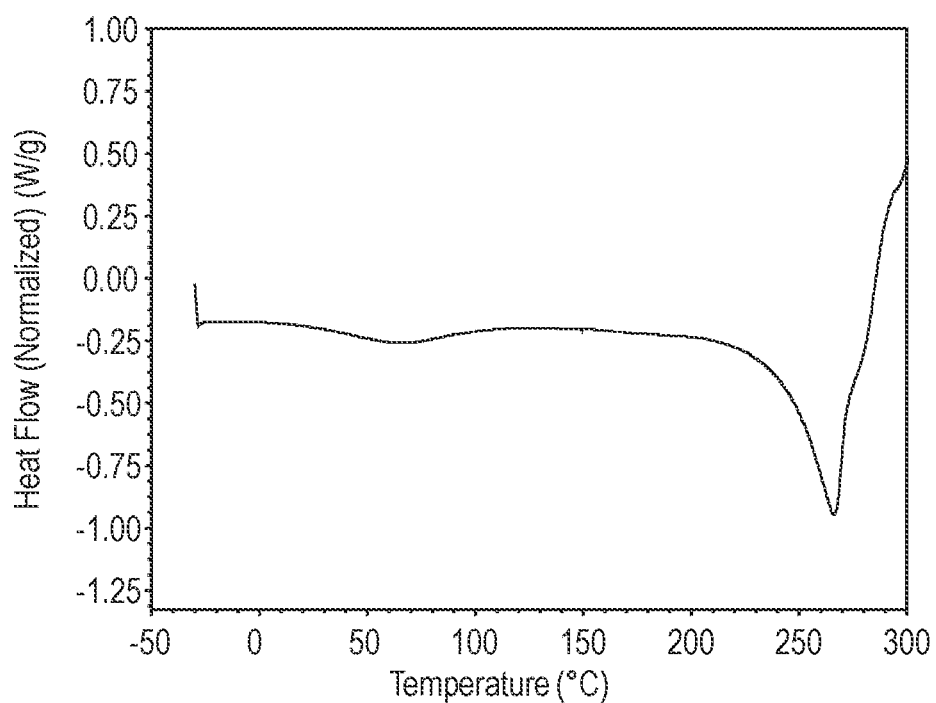
FIG. 14 shows DSC data for crystalline hydrochloride salt Form V of Compound 1.
Figure 15:
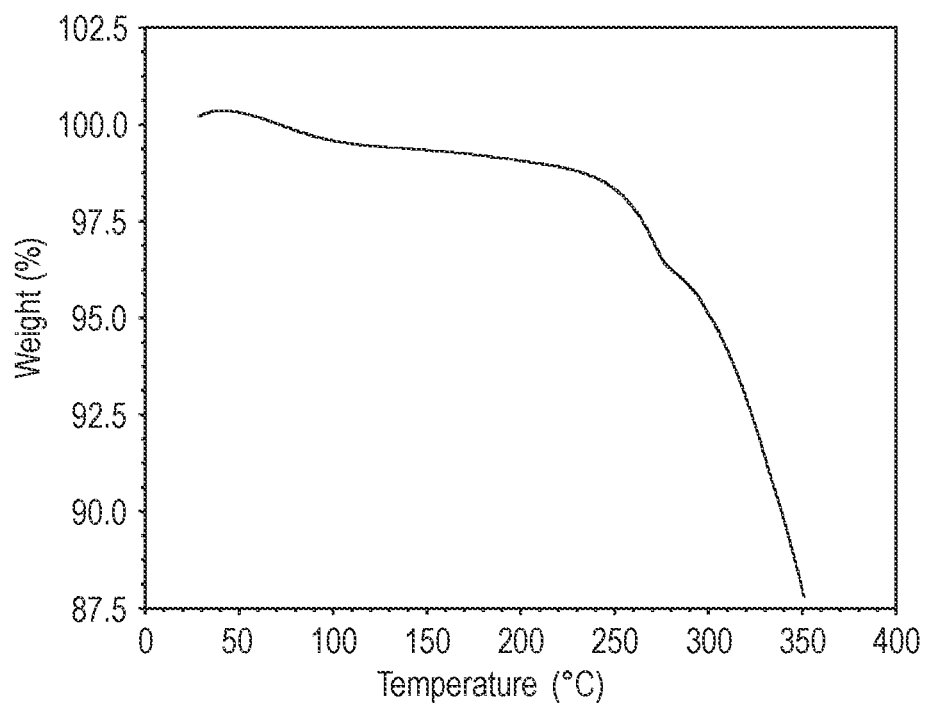
FIG. 15 shows TGA data for crystalline hydrochloride salt Form V of Compound 1.

The crystalline form of hydrochloride salt Form V prepared above was characterized by proton NMR, X-ray powder diffraction (XRPD) data (FIG. 13), DSC (FIG. 14), and TGA (FIG. 15).

NMR: $^1$H NMR (400 MHz, DMSO-$d_6$) δ ppm 0.98-1.13 (m, 2H) 1.13-1.26 (m, 2H) 1.35 (d, J=6.61 Hz, 2H) 2.00-2.16 (m, 2H) 2.82-3.03 (m, 1H) 3.03-3.22 (m, 1H) 3.22-3.38 (m, 1H) 3.39-3.58 (m, 1H) 3.58-3.68 (m, 1H) 4.04 (br d, J=13.85 Hz, 3H) 4.15 (br d, J=12.57 Hz, 2H) 4.23-4.39 (m, 3H) 4.94 (br s, 2H) 5.66-5.88 (m, 2H) 6.07-6.31 (m, 2H) 6.65-6.92 (m, 4H) 7.27 (td, J=8.26, 7.14 Hz, 2H) 7.64 (br s, 1H) 8.22-8.42 (m, 2H) 8.48-8.71 (m, 2H) 10.30 (br s, 1H).

TABLE 5

XRPD data of the Crystalline Hydrochloride Salt Form V of Compound 1
XRPD Peak Table:

| Pos. [°2Th.] | Rel. Int. [%] |
| --- | --- |
| 6.0 | 38.97 |
| 7.9 | 75.66 |
| 9.1 | 5.22 |
| 9.9 | 32.42 |
| 12.0 | 60.98 |
| 12.4 | 12.14 |
| 12.7 | 30.08 |
| 13.2 | 26.24 |
| 13.8 | 100.00 |
| 14.7 | 23.25 |
| 15.4 | 36.73 |
| 15.7 | 37.68 |
| 17.2 | 15.67 |
| 17.3 | 18.79 |
| 18.1 | 11.02 |
| 18.5 | 9.82 |
| 18.9 | 74.01 |
| 19.5 | 3.98 |
| 19.8 | 9.13 |
| 20.1 | 14.79 |
| 20.7 | 13.31 |
| 20.9 | 19.86 |
| 21.8 | 14.49 |
| 22.1 | 16.54 |
| 23.0 | 5.50 |
| 23.5 | 28.36 |
| 23.8 | 11.81 |
| 24.1 | 14.47 |
| 24.4 | 7.62 |
| 25.2 | 8.25 |
| 25.8 | 7.01 |
| 26.3 | 5.02 |
| 27.2 | 4.66 |
| 27.5 | 7.27 |
| 27.8 | 19.52 |
| 28.9 | 7.66 |
| 29.7 | 5.27 |
| 30.1 | 4.46 |
| 31.2 | 3.44 |
| 32.2 | 2.59 |
| 33.4 | 5.05 |
| 34.2 | 2.34 |
| 35.1 | 2.59 |
| 36.3 | 3.00 |
| 37.5 | 4.47 |
| 39.4 | 1.49 |

Example 6: Preparation of Crystalline Hydrochloride Salt Form VI

The crystalline hydrochloride salt Form VI was prepared by slurry of Compound 1 and HCl in p-dioxane at various temperatures.

DSC: endotherm of about 273° C.; TGA: comprising a weight loss of about 4% when heated from about 25° C. to about 250° C.

Figure 17:
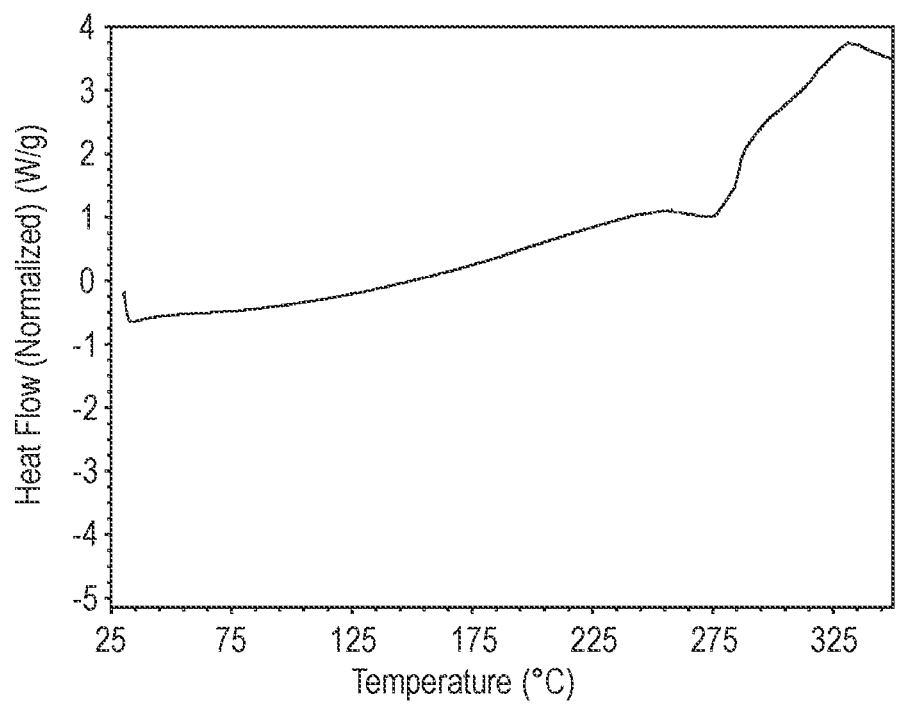
FIG. 17 shows DSC data for crystalline hydrochloride salt Form VI of Compound 1.
Figure 18:
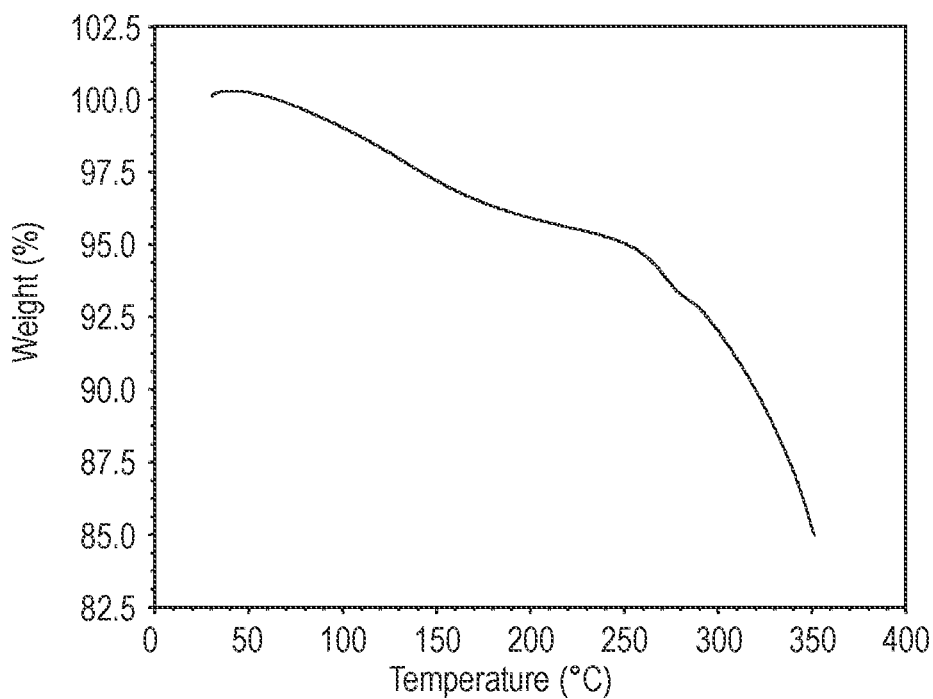
FIG. 18 shows TGA data for crystalline hydrochloride salt Form VI of Compound 1.

The crystalline hydrochloride salt Form VI prepared above was characterized by proton NMR, X-ray powder diffraction (XRPD) data (FIG. 16), DSC (FIG. 17), and TGA (FIG. 18).

NMR: $^1$H NMR (400 MHz, DMSO-$d_6$) δ ppm 1.01-1.15 (m, 3H) 1.22 (d, J=6.82 Hz, 3H) 1.35 (d, J=6.82 Hz, 3H) 2.10 (s, 2H) 2.83-3.04 (m, 1H) 3.04-3.21 (m, 1H) 3.27 (br d, J=11.51 Hz, 1H) 3.44-3.56 (m, 1H) 3.87-4.09 (m, 2H) 4.15 (br d, J=13.21 Hz, 1H) 4.22-4.47 (m, 3H) 4.95 (br s, 1H) 5.64-5.87 (m, 1H) 6.21 (br d, J=16.84 Hz, 1H) 6.65-6.92 (m, 3H) 7.27 (td, J=8.31, 7.03 Hz, 1H) 7.69 (br s, 1H) 8.22-8.48 (m, 1H) 8.49-8.67 (m, 1H) 10.32 (br s, 1H).

TABLE 6

XRPD data of the Crystalline Hydrochloride Salt Form VI of Compound 1
XRPD Peak Table:

| Pos. [°2Th.] | Rel. Int. [%] |
| --- | --- |
| 6.0 | 11.92 |
| 7.7 | 81.53 |
| 9.0 | 3.76 |
| 10.0 | 25.10 |
| 12.1 | 44.38 |
| 12.5 | 14.99 |
| 12.9 | 7.35 |
| 13.1 | 10.36 |
| 13.7 | 93.86 |
| 14.5 | 23.37 |
| 15.2 | 24.88 |
| 15.4 | 11.26 |

TABLE 6-continued

XRPD data of the Crystalline Hydrochloride Salt Form VI of Compound 1
XRPD Peak Table:

| Pos. [°2Th.] | Rel. Int. [%] |
|---|---|
| 15.9 | 31.43 |
| 16.9 | 9.76 |
| 17.2 | 17.51 |
| 18.1 | 25.51 |
| 18.6 | 19.94 |
| 19.0 | 100.00 |
| 20.1 | 15.70 |
| 20.3 | 17.56 |
| 20.9 | 29.68 |
| 21.5 | 9.07 |
| 22.0 | 15.04 |
| 22.3 | 11.37 |
| 22.9 | 11.51 |
| 23.2 | 11.30 |
| 23.6 | 36.88 |
| 24.3 | 24.45 |
| 24.8 | 7.40 |
| 25.4 | 3.83 |
| 26.7 | 9.13 |
| 27.3 | 6.92 |
| 27.5 | 16.62 |
| 28.1 | 5.43 |
| 28.7 | 7.61 |
| 29.7 | 8.09 |
| 30.0 | 5.87 |
| 30.7 | 5.33 |
| 31.5 | 5.71 |
| 33.2 | 5.62 |
| 34.6 | 3.10 |
| 35.5 | 1.01 |
| 36.1 | 2.32 |
| 36.6 | 3.04 |
| 37.1 | 3.41 |
| 37.7 | 1.42 |
| 38.4 | 1.58 |

Example 7: Preparation of Crystalline Hydrochloride Salt Form VII (Isostructural ETOH Hemi-Solvate) of Compound 1

The crystalline hydrochloride salt Form VII of Compound 1 was prepared by crash precipitation from a solution of Compound 1 and HCl in EtOH with the anti-solvent heptane or MTBE.

DSC endotherm onset of about 259° C.

TGA: comprising an approximately negligible weight loss when heated from about 25° C. to about 250° C.

Figure 20:
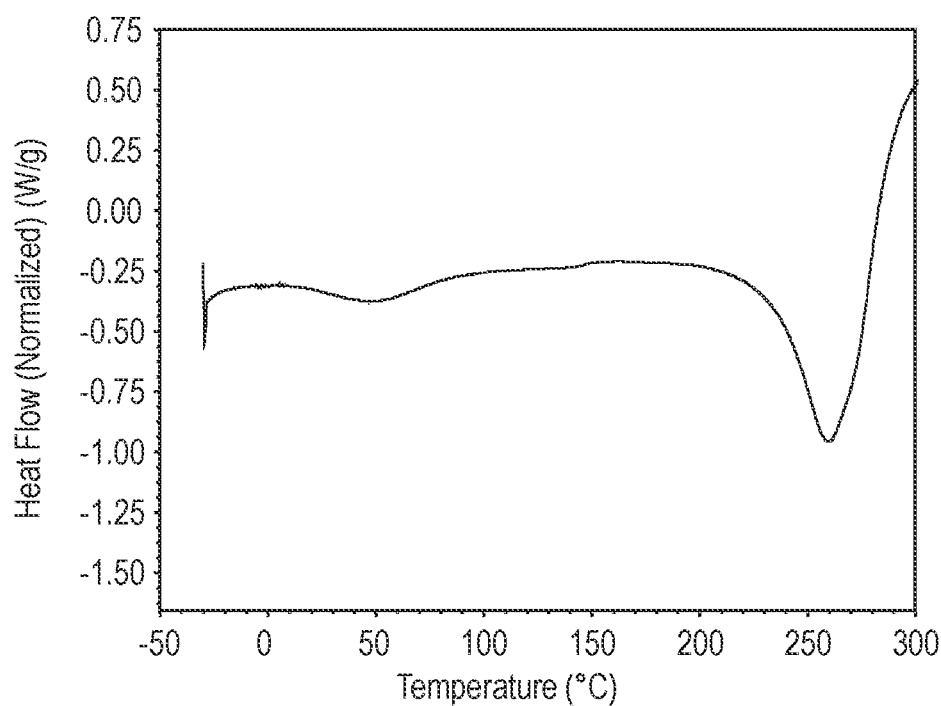
FIG. 20 shows DSC data for the crystalline hydrochloride salt Form VII of Compound 1.
Figure 21:
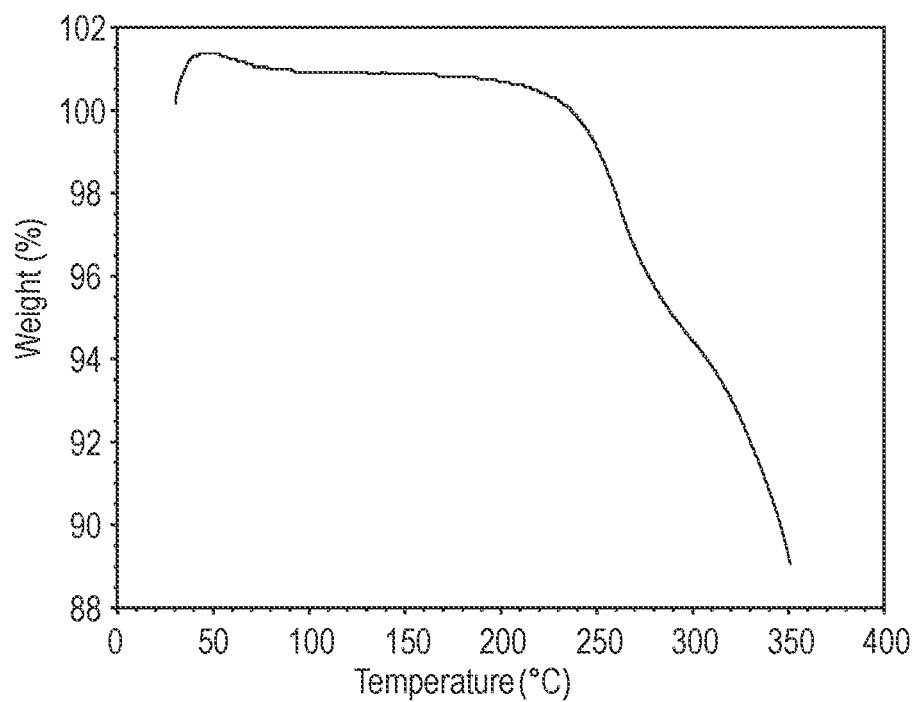
FIG. 21 shows TGA data for crystalline hydrochloride salt Form VII of Compound 1.

The crystalline Hydrochloride Salt Form VII of Compound 1 prepared above was characterized by proton NMR, X-ray powder diffraction (XRPD) data (FIG. 19), DSC (FIG. 20), and TGA (FIG. 21).

$^1$H NMR (400 MHz, DMSO-d$_6$) δ ppm 1.00-1.13 (m, 2H) 1.21 (br d, J=6.82 Hz, 2H) 1.35 (d, J=6.61 Hz, 2H) 2.09 (br s, 2H) 2.82-3.04 (m, 1H) 3.04-3.22 (m, 1H) 3.22-3.36 (m, 1H) 3.36-3.58 (m, 2H) 3.58-3.68 (m, 1H) 3.90-4.09 (m, 2H) 4.15 (br d, J=13.43 Hz, 1H) 4.22-4.47 (m, 2H) 4.94 (br s, 1H) 5.68-5.81 (m, 1H) 6.21 (br d, J=16.84 Hz, 1H) 6.65-6.92 (m, 3H) 7.15-7.40 (m, 1H) 7.67 (br s, 1H) 8.15-8.40 (m, 1H) 8.61 (br d, J=5.33 Hz, 1H) 10.31 (br s, 1H).

TABLE 7

XRPD data of the Crystalline Hydrochloride Salt Form VII of Compound 1
XRPD Peak Table:

| Pos. [°2Th.] | Rel. Int. [%] |
|---|---|
| 6.01 | 31.40 |
| 7.80 | 65.84 |
| 9.03 | 4.35 |
| 9.93 | 24.06 |
| 12.03 | 57.65 |
| 12.36 | 12.98 |
| 12.60 | 19.68 |
| 13.20 | 21.06 |
| 13.76 | 100.00 |
| 14.64 | 19.52 |
| 15.36 | 31.52 |
| 15.77 | 24.56 |
| 15.91 | 22.05 |
| 17.06 | 9.79 |
| 17.28 | 16.40 |
| 17.66 | 3.16 |
| 18.08 | 9.15 |
| 18.92 | 68.46 |
| 20.13 | 16.24 |
| 20.56 | 10.22 |
| 20.86 | 25.29 |
| 21.67 | 8.88 |
| 21.98 | 14.73 |
| 23.27 | 12.74 |
| 23.50 | 25.44 |
| 23.60 | 26.55 |
| 24.34 | 15.61 |
| 24.89 | 5.65 |
| 25.64 | 4.86 |
| 26.40 | 3.87 |
| 27.30 | 6.58 |
| 27.72 | 20.42 |
| 28.80 | 9.64 |
| 29.75 | 6.88 |
| 30.99 | 4.45 |
| 31.87 | 2.57 |
| 33.32 | 6.21 |
| 34.31 | 2.28 |
| 34.84 | 2.34 |
| 35.67 | 1.00 |
| 36.17 | 1.85 |
| 36.34 | 1.83 |
| 37.35 | 3.89 |
| 38.34 | 1.06 |
| 38.89 | 1.29 |

Example 8: Preparation of Crystalline Phosphate Salt Form I of Compound 1

The crystalline phosphate salt Form I was prepared by charging Compound 1 and H$_3$PO$_4$ (0.9:1.0 mol/mol) with 4 mL of MEK then slurry for 24 h at 55° C.

DSC 217° C., TGA comprising a weight loss of about 2.5% when heated from about 25° C. to about 200° C.

Figure 23:
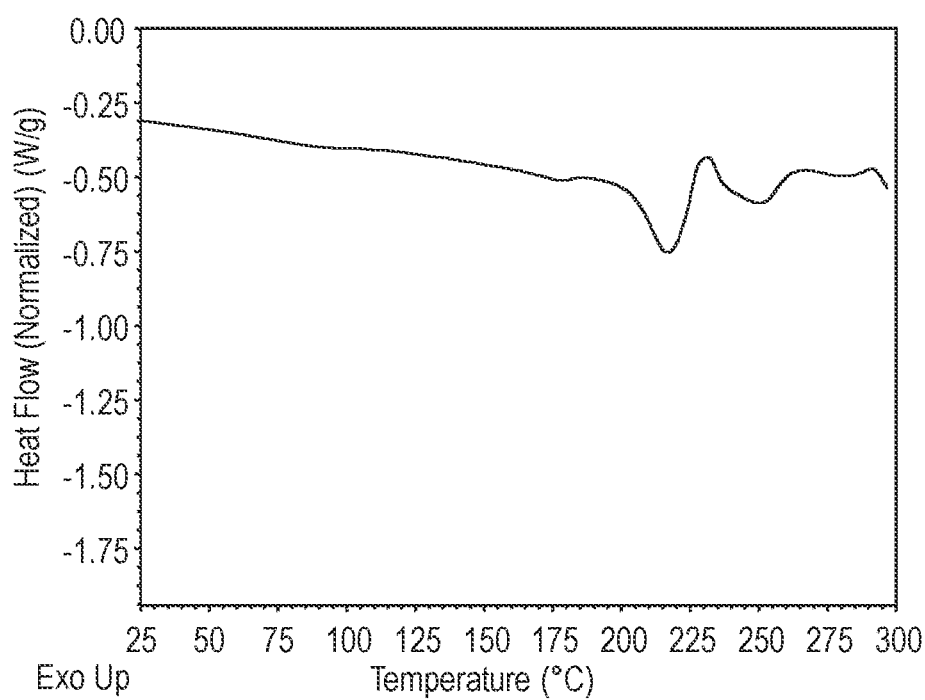
FIG. 23 shows DSC data for the crystalline phosphate salt Form I of Compound 1.
Figure 24:
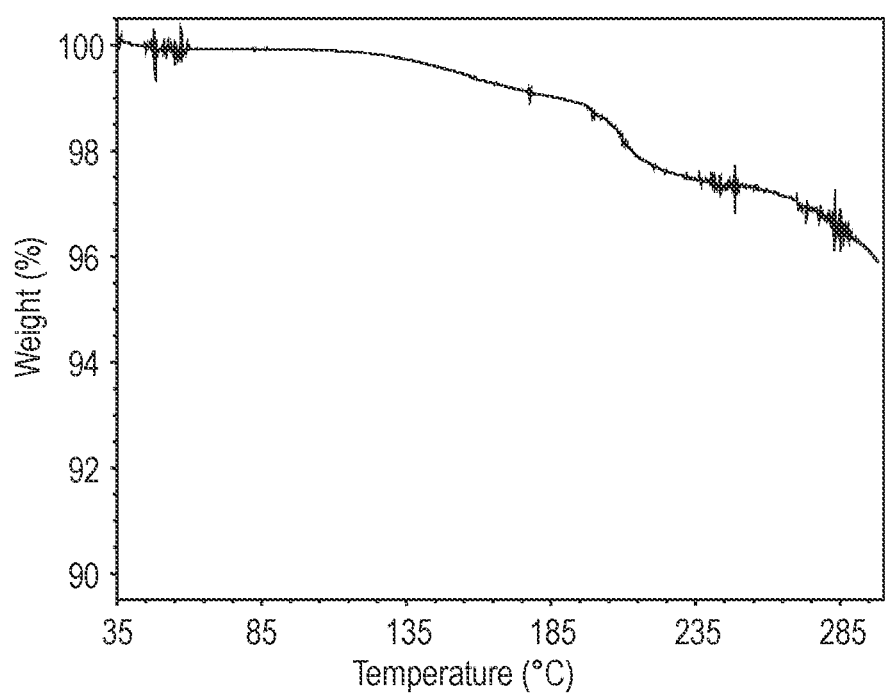
FIG. 24 shows TGA data for the crystalline phosphate salt Form I of Compound 1.

The crystalline form of the phosphate salt Form I prepared above was characterized by proton NMR, X-ray powder diffraction (XRPD) data (FIG. 22), DSC (FIG. 23), and TGA (FIG. 24).

$^1$H NMR (500 MHz, DMSO-d$_6$) δ ppm 0.88-0.97 (m, 2H) 1.07 (d, J=6.75 Hz, 2H) 1.34 (d, J=6.75 Hz, 2H) 1.90 (s, 2H) 2.67-2.76 (m, 1H) 3.14 (br t, J=10.90 Hz, 1H) 3.36-3.59 (m, 1H) 3.59-3.67 (m, 1H) 3.94-4.08 (m, 1H) 4.08-4.22 (m, 1H) 4.22-4.36 (m, 2H) 4.40 (br d, J=13.23 Hz, 1H) 4.90 (br s, 1H) 5.67-5.85 (m, 1H) 6.20 (br dd, J=16.48, 7.14 Hz, 1H) 6.64-6.77 (m, 2H) 6.78-6.93 (m, 1H) 7.13-7.21 (m, 1H) 7.27 (td, J=8.30, 7.01 Hz, 1H) 8.20-8.34 (m, 1H) 8.38 (d, J=4.67 Hz, 1H) 10.17 (br s, 1H)

TABLE 8

XRPD data of the Crystalline Phosphate Salt Form I of Compound 1
XRPD Peak Table:

| Pos. [°2Th.] | Rel. Int. [%] |
|---|---|
| 6.0 | 34.28 |
| 8.7 | 43.53 |
| 10.9 | 28.26 |
| 11.8 | 25.60 |
| 13.7 | 57.01 |
| 14.5 | 50.56 |
| 15.1 | 69.14 |
| 16.3 | 32.09 |
| 17.2 | 100.00 |
| 18.1 | 32.49 |
| 18.8 | 32.17 |
| 19.1 | 82.38 |
| 19.6 | 74.01 |
| 21.4 | 91.01 |
| 22.3 | 42.77 |
| 23.2 | 34.79 |
| 24.0 | 44.04 |
| 25.6 | 39.14 |
| 26.3 | 40.81 |
| 26.7 | 46.15 |
| 27.4 | 53.84 |
| 28.3 | 21.35 |
| 29.6 | 34.71 |
| 30.4 | 16.91 |
| 31.8 | 19.24 |
| 32.7 | 21.49 |
| 34.0 | 5.72 |
| 35.1 | 7.22 |
| 36.1 | 4.11 |
| 37.2 | 5.24 |
| 38.9 | 8.58 |
| 39.9 | 7.08 |
| 41.0 | 7.54 |

Example 9: Preparation of the Crystalline Mesylate Salt Form I of Compound 1

The crystalline mesylate salt Form I was prepared by charging 100 mg of Compound 1 with 1 eq methanesulfonic acid in 4 mL EtOAc then slurry for 24 h at RT.

Figure 26:
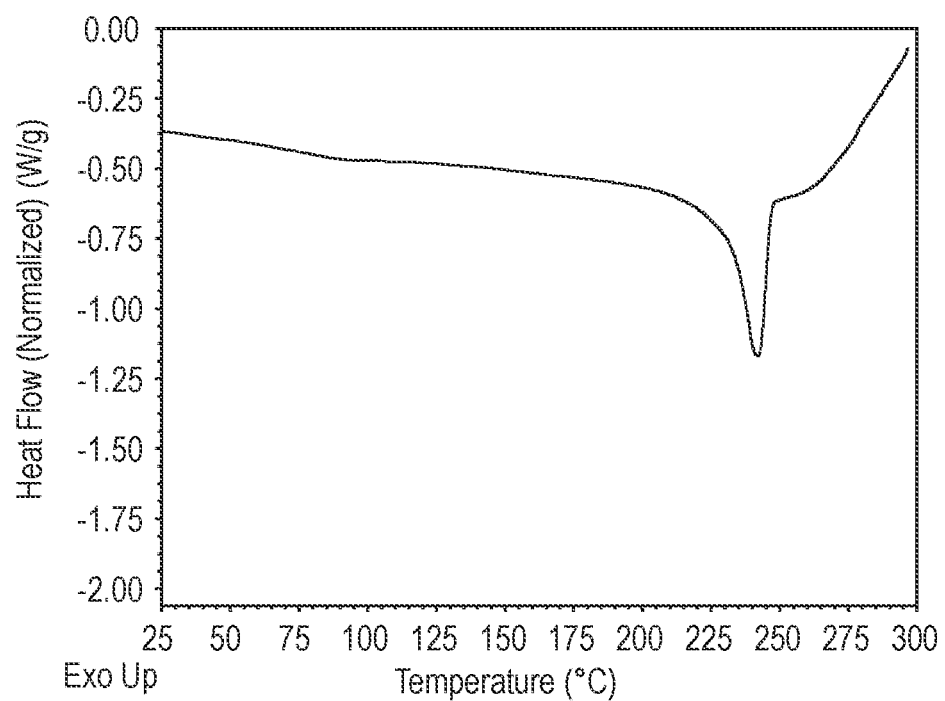
FIG. 26 shows DSC data for the crystalline mesylate salt Form I of Compound 1.
Figure 27:
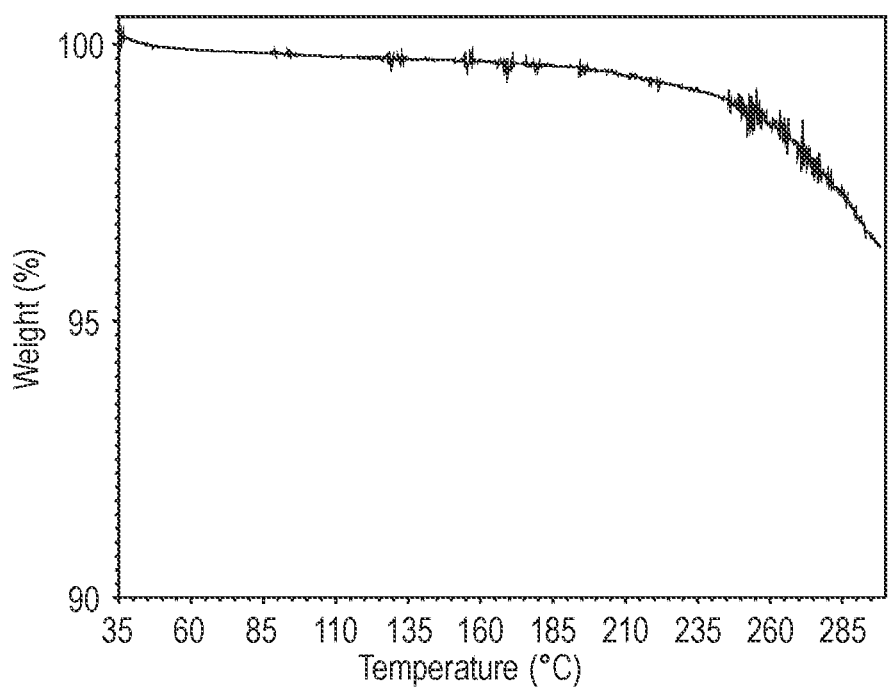
FIG. 27 shows TGA data for the crystalline mesylate salt Form I of Compound 1.

The crystalline form of the mesylate salt Form I prepared above was characterized by proton NMR, X-ray powder diffraction (XRPD) data (FIG. 25), DSC (FIG. 26), and TGA (FIG. 27).

DSC onset of about 242° C., TGA comprising a weight loss of about 0.8% when heated from about 25° C. to about 200° C.

$^1$H NMR (500 MHz, DMSO-$d_6$) δ ppm 0.95-1.10 (m, 4H) 1.10-1.25 (m, 4H) 1.35 (d, J=6.75 Hz, 3H) 2.07 (br s, 3H) 2.30-2.36 (m, 3H) 2.93 (br s, 1H) 3.15 (br t, J=11.03 Hz, 1H) 3.27 (br d, J=10.38 Hz, 1H) 3.41-3.58 (m, 1H) 3.58-3.69 (m, 1H) 3.73 (br s, 1H) 3.88-4.09 (m, 1H) 4.10-4.22 (m, 1H) 4.22-4.52 (m, 3H) 4.70-5.39 (m, 2H) 5.39-6.13 (m, 3H) 6.13-6.26 (m, 1H) 6.65-6.77 (m, 3H) 6.78-6.93 (m, 1H) 7.23-7.32 (m, 1H) 7.62 (br s, 1H) 8.23-8.37 (m, 1H) 8.60 (br s, 1H) 10.24 (br s, 1H).

TABLE 9

XRPD data of crystalline Mesylate Salt Form I of Compound 1:
XRPD Peak Table:

| Pos. [°2Th.] | Rel. Int. [%] |
|---|---|
| 7.6 | 100.00 |
| 8.7 | 17.19 |
| 9.8 | 70.56 |
| 12.7 | 16.30 |
| 14.6 | 67.03 |
| 15.2 | 66.01 |
| 15.8 | 73.78 |
| 17.4 | 40.66 |
| 19.0 | 72.38 |
| 19.6 | 86.48 |
| 20.5 | 89.77 |
| 23.2 | 38.71 |
| 25.0 | 27.78 |
| 28.9 | 28.20 |
| 38.8 | 10.09 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the disclosure. It is intended, therefore, that the invention be defined by the scope of the claims that follow and that such claims be interpreted as broadly as is reasonable.

What is claimed is:

1. A compound, wherein the compound is a crystalline hydrochloride salt of the M atropisomer of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2 (1H)-one.

2. The compound of claim 1, wherein the compound is characterized by an x-ray powder diffraction pattern substantially as shown in FIG. 1 as measured by x-ray powder diffraction using an x-ray wavelength of 1.54 Å.

3. The compound of claim 1, wherein the compound is characterized by an x-ray powder diffraction pattern comprising, at least five peaks selected from 6.6, 8.9, 10.9, 13.7, 14.2, 15.1, 18.0, 19.0, and 21.1±0.2 degrees 2 theta as measured by x-ray powder diffraction using an x-ray wavelength of 1.54 Å.

4. The compound of claim 1, wherein the compound is characterized by an x-ray powder diffraction pattern comprising peaks at 8.9, 10.9, and 14.2±0.2 degrees 2 theta as measured by x-ray powder diffraction using an x-ray wavelength of 1.54 Å.

5. The compound of claim 1, wherein the compound is characterized by an x-ray powder diffraction pattern substantially as shown in FIG. 4 as measured by x-ray powder diffraction using an x-ray wavelength of 1.54 Å.

6. The compound of claim 1, wherein the compound is characterized by an x-ray powder diffraction pattern comprising at least seven peaks selected from 6.0, 6.3, 8.2, 10.6, 11.2, 12.7, 13.6, 14.3, 16.1, 16.5, 17.2, 21.4, and 21.6±0.2 degrees 2 theta as measured by x-ray powder diffraction using an x-ray wavelength of 1.54 Å.

7. The compound of claim 1, wherein the compound is characterized by an x-ray powder diffraction pattern comprising peaks at 6.3, 8.2, 10.6, and 16.1±0.2 degrees 2 theta as measured by x-ray powder diffraction using an x-ray wavelength of 1.54 Å.

8. The compound of claim 1, wherein the compound is characterized by an x-ray powder diffraction pattern substantially as shown in FIG. 7 as measured by x-ray powder diffraction using an x-ray wavelength of 1.54 Å.

9. The compound of claim 1, wherein the compound is characterized by an x-ray powder diffraction pattern comprising at least seven peaks selected from 6.4, 8.4, 11.0, 11.2, 12.7, 13.6, 13.9, 15.0, 15.6, 16.6, 16.7, 16.8, and 21.2±0.2 degrees 2 theta as measured by x-ray powder diffraction using an x-ray wavelength of 1.54 Å.

10. The compound of claim 1, wherein the compound is characterized by an x-ray powder diffraction pattern comprising peaks at 6.4, 8.4, 11.0, and 15.6±0.2 degrees 2 theta as measured by x-ray powder diffraction using an x-ray wavelength of 1.54 Å.

11. The compound of claim 1, wherein the compound is characterized by an x-ray powder diffraction pattern substantially as shown in FIG. 10 as measured by x-ray powder diffraction using an x-ray wavelength of 1.54 Å.

12. The compound of claim 1, wherein the compound is characterized by an x-ray powder diffraction pattern comprising at least five peaks, selected from 5.6, 6.5, 8.5, 11.3, 12.8, 13.6, 14.0, 14.1, 15.0, 16.7, 17.8, and 18.4±0.2 degrees 2 theta as measured by x-ray powder diffraction using an x-ray wavelength of 1.54 Å.

13. The compound of claim 1, wherein the compound is characterized by an x-ray powder diffraction pattern comprising peaks at 5.6, 6.5, and 8.5±0.2 degrees 2 theta as measured by x-ray powder diffraction using an x-ray wavelength of 1.54 Å.

14. The compound of claim 1, wherein the compound is characterized by an x-ray powder diffraction pattern substantially as shown in FIG. 13 as measured by x-ray powder diffraction using an x-ray wavelength of 1.54 Å.

15. The compound of claim 1, wherein the compound is characterized by an x-ray powder diffraction pattern comprising at least seven peaks selected from 6.0, 7.9, 9.1, 9.9, 12.0, 12.4, 12.7, 13.2, 13.8, 14.7, 15.4, 15.7, and 18.9±0.2 degrees 2 theta as measured by x-ray powder diffraction using an x-ray wavelength of 1.54 Å.

16. The compound of claim 1, wherein the compound is characterized by an x-ray powder diffraction pattern comprising peaks at 7.9, 9.9, 13.8, and 15.7±0.2 degrees 2 theta as measured by x-ray powder diffraction using an x-ray wavelength of 1.54 Å.

17. The compound of claim 1, wherein the compound is characterized by an x-ray powder diffraction pattern substantially as shown in FIG. 16 as measured by x-ray powder diffraction using an x-ray wavelength of 1.54 Å.

18. The compound of claim 1, wherein the compound is characterized by an x-ray powder diffraction pattern comprising at least five peaks selected from 6.0, 7.7, 10.0, 12.1, 12.5, 13.7, 14.5, 15.2, 15.9, 18.1, 19.0, and 20.9±0.2 degrees 2 theta as measured by x-ray powder diffraction using an x-ray wavelength of 1.54 Å.

19. The compound of claim 1, wherein the compound is characterized by an x-ray powder diffraction pattern comprising peaks at 7.7, 10.0, and 15.9±0.2 degrees 2 theta as measured by x-ray powder diffraction using an x-ray wavelength of 1.54 Å.

20. The compound of claim 1, wherein the compound is characterized by an x-ray powder diffraction pattern substantially as shown in FIG. 19 as measured by x-ray powder diffraction using an x-ray wavelength of 1.54 Å.

21. The compound of claim 1, wherein the compound is characterized by an x-ray powder diffraction pattern comprising at least seven peaks selected from 6.0, 7.8, 9.0, 9.9, 12.0, 12.6, 13.2, 13.8, 14.6, 15.4, 15.8, 15.9, 18.9, 20.1, 20.6, and 20.9±0.2 degrees 2 theta as measured by x-ray powder diffraction using an x-ray wavelength of 1.54 Å.

22. The compound of claim 1, wherein the compound is characterized by an x-ray powder diffraction pattern comprising peaks at 7.8, 9.9, 13.2, and 14.6±0.2 degrees 2 theta as measured by x-ray powder diffraction using an x-ray wavelength of 1.54 Å.

23. A compound, wherein the compound is a crystalline phosphate salt of the M atropisomer of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2 (1H)-one.

24. The compound of claim 23, wherein the compound is characterized by an x-ray powder diffraction pattern substantially as shown in FIG. 22 as measured by x-ray powder diffraction using an x-ray wavelength of 1.54 Å.

25. The compound of claim 23, wherein the compound is characterized by an x-ray powder diffraction pattern comprising at least seven peaks selected from 6.0, 8.7, 10.9, 11.8, 13.7, 14.5, 15.1, 17.2, 19.1, 19.6, 21.4, 24.0, 25.6, 26.3, 26.7, and 27.4±0.2 degrees 2 theta as measured by x-ray powder diffraction using an x-ray wavelength of 1.54 Å.

26. The compound of claim 23, wherein the compound is characterized by an x-ray powder diffraction pattern comprising peaks at 8.7, 13.7, 14.5, 17.2 and 19.1±0.2 degrees 2 theta as measured by x-ray powder diffraction using an x-ray wavelength of 1.54 Å.

27. A compound, wherein the compound is a crystalline mesylate salt of the M atropisomer of 6-fluoro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2 (1H)-one.

28. The compound of claim 27, wherein the compound is characterized by an x-ray powder diffraction pattern substantially as shown in FIG. 25 as measured by x-ray powder diffraction using an x-ray wavelength of 1.54 Å.

29. The compound of claim 27, wherein the compound is characterized by an x-ray powder diffraction pattern comprising at least seven peaks selected from 7.6, 9.8, 14.6, 15.2, 15.8, 19.0, 19.6, 20.5, and 23.2±0.2 degrees 2 theta as measured by x-ray powder diffraction using an x-ray wavelength of 1.54 Å.

30. The compound of claim 27, wherein the compound is characterized by an x-ray powder diffraction pattern comprising peaks at 7.6, 9.8, 15.8, 19.6 and 20.5±0.2 degrees 2 theta as measured by x-ray powder diffraction using an x-ray wavelength of 1.54 Å.

31. A pharmaceutical composition comprising the compound of claim 1 and a pharmaceutically acceptable excipient.

32. A pharmaceutical composition comprising the compound of claim 4 and a pharmaceutically acceptable excipient.

33. A pharmaceutical composition comprising the compound of claim 7 and a pharmaceutically acceptable excipient.

34. A pharmaceutical composition comprising the compound of claim 10 and a pharmaceutically acceptable excipient.

35. A pharmaceutical composition comprising the compound of claim 13 and a pharmaceutically acceptable excipient.

36. A pharmaceutical composition comprising the compound of claim 16 and a pharmaceutically acceptable excipient.

37. A pharmaceutical composition comprising the compound of claim 19 and a pharmaceutically acceptable excipient.

38. A pharmaceutical composition comprising the compound of claim 22 and a pharmaceutically acceptable excipient.

39. A pharmaceutical composition comprising the compound of claim 23 and a pharmaceutically acceptable excipient.

40. A pharmaceutical composition comprising the compound of claim 26 and a pharmaceutically acceptable excipient.

41. A pharmaceutical composition comprising the compound of claim 27 and a pharmaceutically acceptable excipient.

42. A pharmaceutical composition comprising the compound of claim 30 and a pharmaceutically acceptable excipient.

43. A method of treating a cancer having a KRAS G12C mutation in a human patient in need thereof, the method comprising administering to the human patient a therapeutically effective amount of the compound of claim 1, wherein the cancer is non-small cell lung cancer, small intestine cancer, appendix cancer, colorectal cancer, endometrial cancer, pancreatic cancer, skin cancer, gastric cancer, nasal cavity cancer, bile duct cancer, or brain tumor.

44. The method of claim 43, wherein the cancer is non-small cell lung cancer.

45. The method of claim 43, wherein the cancer is colorectal cancer.

46. The method of claim 43, wherein the cancer is pancreatic cancer.

47. A method of treating a cancer having a KRAS G12C mutation in a human patient in need thereof, the method comprising administering to the human patient a therapeutically effective amount of the compound of claim 23, wherein the cancer is non-small cell lung cancer, small intestine cancer, appendix cancer, colorectal cancer, endometrial cancer, pancreatic cancer, skin cancer, gastric cancer, nasal cavity cancer, bile duct cancer, or brain tumor.

48. The method of claim 47, wherein the cancer is non-small cell lung cancer.

49. The method of claim 47, wherein the cancer is colorectal cancer.

50. The method of claim 47, wherein the cancer is pancreatic cancer.

51. A method of treating a cancer having a KRAS G12C mutation in a human patient in need thereof, the method comprising administering to the human patient a therapeutically effective amount of the compound of claim 27, wherein the cancer is non-small cell lung cancer, small intestine cancer, appendix cancer, colorectal cancer, endometrial cancer, pancreatic cancer, skin cancer, gastric cancer, nasal cavity cancer, bile duct cancer, or brain tumor.

52. The method of claim 51, wherein the cancer is non-small cell lung cancer.

53. The method of claim 51, wherein the cancer is colorectal cancer.

54. The method of claim 51, wherein the cancer is pancreatic cancer.

* * * * *

UNITED STATES PATENT AND TRADEMARK OFFICE
CERTIFICATE OF CORRECTION

| | | |
|---|---|---|
| PATENT NO. | : 12,252,486 B2 | Page 1 of 1 |
| APPLICATION NO. | : 17/612717 | |
| DATED | : March 18, 2025 | |
| INVENTOR(S) | : Chaves et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this
Sixteenth Day of December, 2025

John A. Squires
*Director of the United States Patent and Trademark Office*